(12) United States Patent
Begemann

(10) Patent No.: US 11,279,942 B2
(45) Date of Patent: Mar. 22, 2022

(54) MAIZE RBCS7A PROMOTER FOR EXPRESSING A FERREDOXIN-THIOREDOXIN REDUCTASE IN A PLANT

(71) Applicant: BENSON HILL, INC., St. Louis, MO (US)

(72) Inventor: Matthew Begemann, St. Louis, MO (US)

(73) Assignee: Benson Hill, Inc., St. Louis, MO (US)

( * ) Notice: Subject to any disclaimer, the term of this patent is extended or adjusted under 35 U.S.C. 154(b) by 149 days.

(21) Appl. No.: 16/629,754

(22) PCT Filed: Jul. 12, 2018

(86) PCT No.: PCT/IB2018/055168
§ 371 (c)(1),
(2) Date: Jan. 9, 2020

(87) PCT Pub. No.: WO2019/012483
PCT Pub. Date: Jan. 17, 2019

(65) Prior Publication Data
US 2021/0147864 A1    May 20, 2021

Related U.S. Application Data

(60) Provisional application No. 62/532,085, filed on Jul. 13, 2017.

(51) Int. Cl.
*C12N 15/82*    (2006.01)
*C12N 9/00*    (2006.01)
*C12N 9/02*    (2006.01)

(52) U.S. Cl.
CPC ....... *C12N 15/8222* (2013.01); *C12N 9/0051* (2013.01); *C12N 15/8261* (2013.01); *C12Y 108/07002* (2013.01)

(58) Field of Classification Search
None
See application file for complete search history.

(56) References Cited

U.S. PATENT DOCUMENTS

2006/0294622 A1* 12/2006 Sosa ............... C07K 14/415
800/286
2007/0011783 A1    1/2007 Jingdon et al.

FOREIGN PATENT DOCUMENTS

| WO | WO 2004/035798 A2 | 4/2004 | |
|----|---|---|---|
| WO | WO 2005/118820 A2 | 12/2005 | |
| WO | WO-2005118820 A2 * | 12/2005 | ......... C12N 15/8271 |
| WO | WO 2016/182847 A1 | 11/2016 | |

OTHER PUBLICATIONS

Wilson, R. K. *Zea mays* cultivar B73 chromosome 4 clone CH201-117E18 (2013) GenBank Accession AC205525.4; pp. 1-39 (Year: 2013).*

* cited by examiner

*Primary Examiner* — Cathy Kingdon Worley
(74) *Attorney, Agent, or Firm* — Womble Bond Dickinson (US) LLP

(57) ABSTRACT

Compositions and methods for improving plant growth are provided herein. The maize RbcS7A promoter is provided which is a developmentally regulated promoter. Polynucleotides encoding ferredoxin-thioredoxin reductase proteins, polypeptides encompassing ferredoxin-thioredoxin reductase proteins, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

15 Claims, No Drawings
Specification includes a Sequence Listing.

SEQUENCE LISTING

<160> NUMBER OF SEQ ID NOS: 106

<210> SEQ ID NO 1
<211> LENGTH: 459
<212> TYPE: DNA
<213> ORGANISM: Zea mays
<220> FEATURE:
<221> NAME/KEY: misc_feature
<222> LOCATION: (1)..(459)
<223> OTHER INFORMATION: Ferredoxin-thioredoxin reductase

<400> SEQUENCE: 1

| | | | | | |
|---|---|---|---|---|---|
| atgacatcca | ccgtcaccac | aaccgttggg | tgcggggggc | tccccgtccg | cccgttgtcg | 60 |
| acagcgacca | gaggacgccc | acgcagatgc | gccgtccgag | cccaggccgc | gggagcggat | 120 |
| gcctccaatg | ataagtcagt | ggaggtcatg | cgcaagttct | ccgagcagta | cgcccgccgc | 180 |
| tccaacactt | tcttctgcgc | cgacaagaca | gtcactgccg | tcgtcatcaa | gggacttgct | 240 |
| gatcacaggg | atactcttgg | agctcctcta | tgcccttgta | ggcattatga | tgacaaagct | 300 |
| gcggaggtag | cacaaggatt | ttggaattgc | ccatgcgtcc | ccatgcgtga | gaggaaggaa | 360 |
| tgccactgta | tgcttttct | tactcccgat | aatgactttg | ctgggaagga | tcaggttatc | 420 |
| tccttcgagg | agatcaaaga | ggcgacatcg | aagttctaa | | | 459 |

<210> SEQ ID NO 2
<211> LENGTH: 152
<212> TYPE: PRT
<213> ORGANISM: Zea mays
<220> FEATURE:
<221> NAME/KEY: MISC_FEATURE
<222> LOCATION: (1)..(152)
<223> OTHER INFORMATION: Ferredoxin-thioredoxin reductase

<400> SEQUENCE: 2

Met Thr Ser Thr Val Thr Thr Thr Val Gly Cys Gly Gly Leu Pro Val
1               5                   10                  15

Arg Pro Leu Ser Thr Ala Thr Arg Gly Arg Pro Arg Arg Cys Ala Val
            20                  25                  30

Arg Ala Gln Ala Ala Gly Ala Asp Ala Ser Asn Asp Lys Ser Val Glu
        35                  40                  45

Val Met Arg Lys Phe Ser Glu Gln Tyr Ala Arg Arg Ser Asn Thr Phe
50                  55                  60

Phe Cys Ala Asp Lys Thr Val Thr Ala Val Val Ile Lys Gly Leu Ala
65                  70                  75                  80

Asp His Arg Asp Thr Leu Gly Ala Pro Leu Cys Pro Cys Arg His Tyr
                85                  90                  95

Asp Asp Lys Ala Ala Glu Val Ala Gln Gly Phe Trp Asn Cys Pro Cys
            100                 105                 110

Val Pro Met Arg Glu Arg Lys Glu Cys His Cys Met Leu Phe Leu Thr
        115                 120                 125

Pro Asp Asn Asp Phe Ala Gly Lys Asp Gln Val Ile Ser Phe Glu Glu
    130                 135                 140

Ile Lys Glu Ala Thr Ser Lys Phe
145                 150

<210> SEQ ID NO 3
<211> LENGTH: 780
<212> TYPE: DNA
<213> ORGANISM: Cauliflower Mosaic Virus
<220> FEATURE:
<221> NAME/KEY: promoter

```
<222> LOCATION: (1)..(780)
<223> OTHER INFORMATION: 2X35S promoter

<400> SEQUENCE: 3
atggtggagc acgacactct cgtctactcc aagaatatca aagatacagt ctcagaagac      60
caaagggcta ttgagacttt tcaacaaagg gtaatatcgg gaaacctcct cggattccat     120
tgcccagcta tctgtcactt catcaaaagg acagtagaaa aggaaggtgg cacctacaaa     180
tgccatcatt gcgataaagg aaaggctatc gttcaagatg cctctgccga cagtggtccc     240
aaagatggac ccccacccac gaggagcatc gtggaaaaag aagacgttcc aaccacgtct     300
tcaaagcaag tggattgatg tgaacatggt ggagcacgac actctcgtct actccaagaa     360
tatcaaagat acagtctcag aagaccaaag gctattgag  acttttcaac aaagggtaat     420
atcgggaaac ctcctcggat tccattgccc agctatctgt cacttcatca aaaggacagt     480
agaaaaggaa ggtggcacct acaaatgcca tcattgcgat aaaggaaagg ctatcgttca     540
agatgcctct gccgacagtg gtcccaaaga tggaccccca cccacgagga gcatcgtgga     600
aaaagaagac gttccaacca cgtcttcaaa gcaagtggat tgatgtgata tctccactga     660
cgtaagggat gacgcacaat cccactatcc ttcgcaagac ccttcctcta tataaggaag     720
ttcatttcat ttggagagga cacgctgaaa tcaccagtct ctctctacaa atctatctct     780

<210> SEQ ID NO 4
<211> LENGTH: 209
<212> TYPE: DNA
<213> ORGANISM: Cauliflower Mosaic Virus
<220> FEATURE:
<221> NAME/KEY: misc_feature
<222> LOCATION: (1)..(209)
<223> OTHER INFORMATION: 35S polyA

<400> SEQUENCE: 4
gatctgtcga tcgacaagct cgagtttctc cataataatg tgtgagtagt tcccagataa      60
gggaattagg gttcctatag gtttcgctc  atgtgttgag catataagaa acccttagta     120
tgtatttgta tttgtaaaat acttctatca ataaaatttc taattcctaa aaccaaaatc     180
cagtactaaa atccagatcc cccgaatta                                       209

<210> SEQ ID NO 5
<211> LENGTH: 798
<212> TYPE: DNA
<213> ORGANISM: Zea mays
<220> FEATURE:
<221> NAME/KEY: promoter
<222> LOCATION: (1)..(798)
<223> OTHER INFORMATION: RbcS7A promoter+5'UTR

<400> SEQUENCE: 5
gatgactgat gacagacgtg gggaattcaa atgcaactct agcgaaagtt catatatttt      60
tcataaatag ctgaggctgg ggtaattatt tttttgtag  aaaaatagaa taggtggaat     120
ggttggggaa ggcgtaggcg ctcgtggacg acgcccgata aagacaaga  ggcggaattg     180 ccatgaattc gaggtagcta agtaaggcgc atatatatgc caaaaaattc tactgtcact     240
ttccaatttc aatgcgctgc caaacaagcc atcctggaaa ctgacttgaa ttcagcccaa     300
ttctgtagat ccaaacaggg ccggcgtcag tgcctcaggt gagagagcag cagacgatgc     360
aaagagccaa aactgcaagc agacgcagcc gaagccgaag ccgaagccca agcccaaaac     420
tgttttgtct ttgcccagaa ccgcgacgag cctaaactgc gcttcctcct atctacaagt     480
```

```
ccctggcaca tcacgcatag tccaaccatg gcgcgcaggc gataaggcga gccacgggga      540
cgcgacatgt ggtggcggac gcgatcagga tagggccagg ctggccgggc gcggccacgg      600
gatctagatg gccactcgtc ccacatccgc ttcgtcctgt cctgtactgc gtcctgcccc      660
caacgagagc cggagccggc catcccgtcg cacactctcc ccctctatat atgccgtcgg      720 tgtggggag cctactacag gacgacccaa gcaagcaagc aagcagcgag tacatacata       780
ctaggcagcc aggcagcc                                                    798

<210> SEQ ID NO 6
<211> LENGTH: 439
<212> TYPE: DNA
<213> ORGANISM: Zea mays
<220> FEATURE:
<221> NAME/KEY: 3'UTR
<222> LOCATION: (1)..(439)
<223> OTHER INFORMATION: ZmRbcS 3'UTR

<400> SEQUENCE: 6
accgcgcccg ccggccgccc cccgccggct agctagctag ctagctcctg cgtgagctag       60
tagctagtgc catgcgtcgt ctctgtcgtt cggttttgct tcgggtcacc gtgtacccctt     120 tgcttgcttg gttcttcttc tccttttttc cttttttttt cttcttttcc ccggccatgg     180
ttcctttgct ttccagcagt tctctgctgg atgtgatgta tccattgttg caatcatggc     240
cttgcattgg ctacctctat acctgctaca aaactactgc aacgcctata tatacttggg     300
gtgaggaaca tgtgaatgca agctccggct atcatataca tgtaatatgg atacaaacta     360
tatatataaa tccgccgagg cgccgacaat actatacgac accgtgttaa gttaatatat     420
aactggtgct ttttattta                                                  439

<210> SEQ ID NO 7
<211> LENGTH: 974
<212> TYPE: DNA
<213> ORGANISM: Zea mays
<220> FEATURE:
<221> NAME/KEY: promoter
<222> LOCATION: (1)..(974)
<223> OTHER INFORMATION: ZmRbcS promoter+5'UTR

<400> SEQUENCE: 7
gagctccctt taatctggcg ctagatctgc atccgcggct tgcaaagata aatggcacat       60
ttagtgtgtt attttgcaat acctttcata gtagatatcc ttaaatgcag ttttaggcat     120
gtttgggtaa ttaaataaca ttttaggag gagttttaga tttacctttc tttcgtgatg      180
actgatgaca gacgtgggga attcaaatgc aactctagcg aaagttcata tattttttcat    240 aaatagctga ggctggggta attattttt ttgtagaaaa atagaatagg tggaatggtt      300
ggggaaggcg taggcgctcg tggacgacgc ccgataaaag acaagaggcg gaattgccat     360
gaattcgagg tagctaagta aggcgcatat atatgccaaa aaattctact gtcactttcc     420
aatttcaatg cgctgccaaa caagccatcc tggaaactga cttgaattca gcccaattct    480
gtagatccaa acagggccgg cgtcagtgcc tcaggtgaga gagcagcaga cgatgcaaag    540
agccaaaact gcaagcagac gcagccgaag ccgaagccga gcccaagcc caaaactgtt    600 ttgtctttgc ccagaaccgc gacgagccta aactgcgctt cctcctatct acaagtccct     660
ggcacatcac gcatagtcca accatggcgc gcaggcgata aggcgcgcca cggggacgcg    720
acatgtggtg gcgacgcga tcaggatagg gccaggctgg ccgggcgcgg ccacgggaga    780
acggtggcca ctcgtcccac atccgcttcg tcctgtcctg tactgcgtcc tgcccccaac     840
```

-continued

| | |
|---|---|
| gagagccgga gccggccatc ccgtcgcaca ctctcccccT ctatatatgc cgtcggtgtg | 900 |
| ggggagccta ctacaggacg acccaagcaa gcaagcaagc agcgagtaca tacatactag | 960 |
| gcagccaggc agcc | 974 |

```
<210> SEQ ID NO 8
<211> LENGTH: 1647
<212> TYPE: DNA
<213> ORGANISM: Synechococcus sp. and Pisum sativum
<220> FEATURE:
<221> NAME/KEY: misc_feature
<222> LOCATION: (1)..(1647)
<223> OTHER INFORMATION: RbcS-ictB
<220> FEATURE:
<221> NAME/KEY: sig_peptide
<222> LOCATION: (1)..(339)
<223> OTHER INFORMATION: P. sativum RbcS signal peptide
<220> FEATURE:
<221> NAME/KEY: misc_feature
<222> LOCATION: (340)..(1647)
<223> OTHER INFORMATION: ictB

<400> SEQUENCE: 8
```

| | |
|---|---|
| atggcttcta tgatttcttc ttctgctgtg acaacagtgt ctagggcttc tagggccag | 60 |
| tctgctgctg tggctccttt cggcggcctc aagtctatga caggcttccc tgtgaagaag | 120 |
| gtgaatacag atattacatc tattacatct aatggcggca gggtgaagtg catgcaggtg | 180 |
| tggcctccta ttggcaagaa gaagttcgag acactctctt acctccctcc tctcacaagg | 240 |
| gatatgacag tgtggcagac actcacattc gctcattacc agcctcagca gtggggccat | 300 |
| tcttctttcc tccataggct cttcggctct tcagggctt ggagggcttc ttctcagctc | 360 |
| ctcgtgtggt ctgaggctct cggcggcttc ctcctcgctg tggtgtacgg ctctgctcct | 420 |
| ttcgtgcctt cttctgctct cggcctcggc ctcgctgcta ttgctgctta ctgggctctc | 480 |
| ctctctctca cagatattga tctcaggcag gctacaccta ttcattggct cgtgctcctc | 540 |
| tactggggcg tggatgctct cgctacaggc ctctctcctg tgagggctgc tgctctcgtg | 600 |
| ggcctcgcta agctcacact ctacctcctc gtgttcgctc tcgctgctag ggtgctcagg | 660 |
| aatcctaggc tcaggtctct cctcttctct gtggtggtga ttacatctct cttcgtgtct | 720 |
| gtgtacggcc tcaatcagtg gatttacggc gtggaggagc tcgctacatg ggtggatagg | 780 |
| aattctgtgg ctgatttcac atctagggtg tactcttacc tcggcaatcc taatctcctc | 840 |
| gctgcttacc tcgtgcctac aacagctttc tctgctgctg ctattggcgt gtggaggggc | 900 |
| tggctcccta agctcctcgc tattgctgct acaggcgctc ttctctctg cctcattctc | 960 |
| acatactcta ggggcggctg gctcggcttc gtggctatga ttttcgtgtg ggctctcctc | 1020 |
| ggcctctact ggttccagcc taggctccct gctccttgga ggaggtggct cttccctgtg | 1080 |
| gtgctcggcg gcctcgtggc tgtgctcctc gtggctgtgc tcggcctcga gcctctcagg | 1140 |
| gtgagggtgc tctctatttt cgtgggcagg gaggattctt ctaataattt caggattaat | 1200 |
| gtgtggctcg ctgtgctcca gatgattcag gataggcctt ggctcggcat tggccctggc | 1260 |
| aatacagctt tcaatctcgt gtaccctctc taccagcagg ctaggttcac agctctctct | 1320 |
| gcttactctg tgcctctcga ggtggctgtg gagggcggcc tcctcggcct cacagctttc | 1380 |
| gcttggctcc tcctcgtgac agctgtgaca gctgtgcgcc aggtgtctag gctcaggagg | 1440 |
| gataggaatc tcaggctttt ctggctcatg gcttctctcg ctggcctcgc tggcatgctc | 1500 |
| ggccatggcc tcttcgatac agtgctctac aggcctgagg cttctacact ctggtggctc | 1560 |

```
tgcattggcg ctattgcttc tttctggcag cctcagcctt ctaagcagct ccctcctgag    1620
gctgagcatt ctgatgagaa gatgtga                                        1647
```

<210> SEQ ID NO 9
<211> LENGTH: 548
<212> TYPE: PRT
<213> ORGANISM: Synechococcus sp. and Pisum sativum
<220> FEATURE:
<221> NAME/KEY: MISC_FEATURE
<222> LOCATION: (1)..(548)
<223> OTHER INFORMATION: RbcS-ictB
<220> FEATURE:
<221> NAME/KEY: MISC_FEATURE
<222> LOCATION: (1)..(113)
<223> OTHER INFORMATION: P. sativum RbcS signal peptide
<220> FEATURE:
<221> NAME/KEY: MISC_FEATURE
<222> LOCATION: (114)..(548)
<223> OTHER INFORMATION: ictB

<400> SEQUENCE: 9

```
Met Ala Ser Met Ile Ser Ser Ala Val Thr Thr Val Ser Arg Ala
1               5                   10                  15

Ser Arg Gly Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Met Thr Val Trp Gln Thr Leu Thr Phe Ala His Tyr Gln Pro Gln
                85                  90                  95

Gln Trp Gly His Ser Ser Phe Leu His Arg Leu Phe Gly Ser Leu Arg
            100                 105                 110

Ala Trp Arg Ala Ser Ser Gln Leu Leu Val Trp Ser Glu Ala Leu Gly
        115                 120                 125

Gly Phe Leu Leu Ala Val Val Tyr Gly Ser Ala Pro Phe Val Pro Ser
    130                 135                 140

Ser Ala Leu Gly Leu Gly Leu Ala Ala Ile Ala Ala Tyr Trp Ala Leu
145                 150                 155                 160

Leu Ser Leu Thr Asp Ile Asp Leu Arg Gln Ala Thr Pro Ile His Trp
                165                 170                 175

Leu Val Leu Leu Tyr Trp Gly Val Asp Ala Leu Ala Thr Gly Leu Ser
            180                 185                 190

Pro Val Arg Ala Ala Ala Leu Val Gly Leu Ala Lys Leu Thr Leu Tyr
        195                 200                 205

Leu Leu Val Phe Ala Leu Ala Ala Arg Val Leu Arg Asn Pro Arg Leu
    210                 215                 220

Arg Ser Leu Leu Phe Ser Val Val Ile Thr Ser Leu Phe Val Ser
225                 230                 235                 240

Val Tyr Gly Leu Asn Gln Trp Ile Tyr Gly Val Glu Glu Leu Ala Thr
                245                 250                 255

Trp Val Asp Arg Asn Ser Val Ala Asp Phe Thr Ser Arg Val Tyr Ser
            260                 265                 270

Tyr Leu Gly Asn Pro Asn Leu Leu Ala Ala Tyr Leu Val Pro Thr Thr
        275                 280                 285

Ala Phe Ser Ala Ala Ala Ile Gly Val Trp Arg Gly Trp Leu Pro Lys
```

```
                290                 295                 300
Leu Leu Ala Ile Ala Ala Thr Gly Ala Ser Ser Leu Cys Leu Ile Leu
305                 310                 315                 320

Thr Tyr Ser Arg Gly Gly Trp Leu Gly Phe Val Ala Met Ile Phe Val
                325                 330                 335

Trp Ala Leu Leu Gly Leu Tyr Trp Phe Gln Pro Arg Leu Pro Ala Pro
                340                 345                 350

Trp Arg Arg Trp Leu Phe Pro Val Val Leu Gly Gly Leu Val Ala Val
                355                 360                 365

Leu Leu Val Ala Val Leu Gly Leu Glu Pro Leu Arg Val Arg Val Leu
370                 375                 380

Ser Ile Phe Val Gly Arg Glu Asp Ser Ser Asn Asn Phe Arg Ile Asn
385                 390                 395                 400

Val Trp Leu Ala Val Leu Gln Met Ile Gln Asp Arg Pro Trp Leu Gly
                405                 410                 415

Ile Gly Pro Gly Asn Thr Ala Phe Asn Leu Val Tyr Pro Leu Tyr Gln
                420                 425                 430

Gln Ala Arg Phe Thr Ala Leu Ser Ala Tyr Ser Val Pro Leu Glu Val
                435                 440                 445

Ala Val Glu Gly Gly Leu Leu Gly Leu Thr Ala Phe Ala Trp Leu Leu
450                 455                 460

Leu Val Thr Ala Val Thr Ala Val Arg Gln Val Ser Arg Leu Arg Arg
465                 470                 475                 480

Asp Arg Asn Pro Gln Ala Phe Trp Leu Met Ala Ser Leu Ala Gly Leu
                485                 490                 495

Ala Gly Met Leu Gly His Gly Leu Phe Asp Thr Val Leu Tyr Arg Pro
                500                 505                 510

Glu Ala Ser Thr Leu Trp Trp Leu Cys Ile Gly Ala Ile Ala Ser Phe
                515                 520                 525

Trp Gln Pro Gln Pro Ser Lys Gln Leu Pro Pro Glu Ala Glu His Ser
530                 535                 540

Asp Glu Lys Met
545

<210> SEQ ID NO 10
<211> LENGTH: 741
<212> TYPE: DNA
<213> ORGANISM: Sorghum bicolor
<220> FEATURE:
<221> NAME/KEY: promoter
<222> LOCATION: (1)..(741)
<223> OTHER INFORMATION: 4xRGCGR promoter

<400> SEQUENCE: 10
gaagcgagtg gcgcgctggc ggatgaggcg gcgagtggcc cggatgcacc ggcgcaggcg    60
agcgaagcga gtggcgcgct ggcggatgag gcggcgagtg gcccggatgc accggcgcag   120
gcgagcgaag cgagtggcgc gctggcggat gaggcggcga gtggcccgga tgcaccggcg   180
caggcgagcg aagcgagtgg cgcgctggcg gatgaggcgg cgagtggccc ggatgcaccg   240
gcgcaggcga gccgcacgcc gccgcccgcc gggcgctcg cgcgcacc gctgccgcct     300 gccgccacac aatgcgagcg cgcgcgcaca cacacacaca ccacccgggc gggggggctg   360
tagtagtaac ggccttgtct tgtcggcacg cgcgcgtccg tgtgtataag gaggcaggcc   420
cgcgacaacg ataagcggca ctcgcacgat caatgtacac attgcccgtc gcgccacca   480 catccagcat cgtcgccagc ctcgccaccc ccgcgccgtc ctcctcctcc ggctccggct   540
```

```
ccggccgccc caggcccagg ctcatccgga acgcccccgt cttcgccgcc ccgccaccg    600 tcgtgtaaac gggacggcgg gcagctgagg agtcaaacga gagagatcga gagaaagaaa   660
gggagggcat ccaccagccc ccggcgataa gaggggagga gagagaggcc agagaagagg   720
aggagaagaa gaagaaatcg a                                            741
```

<210> SEQ ID NO 11
<211> LENGTH: 525
<212> TYPE: DNA
<213> ORGANISM: Zea mays
<220> FEATURE:
<221> NAME/KEY: misc_feature
<222> LOCATION: (1)..(525)
<223> OTHER INFORMATION: GRMZM2G181258

<400> SEQUENCE: 11

```
atggccctcg agacatgctt tagggcctgg gccctccacg ccgcgccagc cgggtccaag    60
gaccgcctcc tcgtgtgttc ctccgggggg aacctcgtcc tgccgtccaa gagggtcgcg   120
gccgcgccac tctccgtcgg cagggtcgcg accgccgcg cccgccatgt gtgccagtcc    180
aaaaatgcgg tcgatgaagt gctcgtcgcg gatgaaaaaa actgggatgg catggtcatg   240
gcgtgtgaga ccccagtgct ggtcgaattc tgggccccat ggtgtgggcc gtgccgcatg   300
attgcgccgg tcatcgacga gctggcgaag gactatgcgg gcaaaattat gtgttgcaaa   360
gtcaatacag acgacagccc gaatgtcgcg tccacctacg gcattaggtc catcccaaca   420
gtgctcatct ttaaaggcgg cgagaagaaa gagagcgtca ttggcgcggt gccaaaaagc   480
acactcacaa ccctcatcga caaatatatc gggtccagct cctga                  525
```

<210> SEQ ID NO 12
<211> LENGTH: 174
<212> TYPE: PRT
<213> ORGANISM: Zea mays
<220> FEATURE:
<221> NAME/KEY: MISC_FEATURE
<222> LOCATION: (1)..(174)
<223> OTHER INFORMATION: GRMZM2G181258

<400> SEQUENCE: 12

```
Met Ala Leu Glu Thr Cys Phe Arg Ala Trp Ala Leu His Ala Ala Pro
1               5                   10                  15

Ala Gly Ser Lys Asp Arg Leu Leu Val Cys Ser Ser Gly Gly Asn Leu
            20                  25                  30

Val Leu Pro Ser Lys Arg Val Ala Ala Pro Leu Ser Val Gly Arg
        35                  40                  45

Val Ala Thr Arg Arg Ala Arg His Val Cys Gln Ser Lys Asn Ala Val
    50                  55                  60

Asp Glu Val Leu Val Ala Asp Glu Lys Asn Trp Asp Gly Met Val Met
65                  70                  75                  80

Ala Cys Glu Thr Pro Val Leu Val Glu Phe Trp Ala Pro Trp Cys Gly
                85                  90                  95

Pro Cys Arg Met Ile Ala Pro Val Ile Asp Glu Leu Ala Lys Asp Tyr
            100                 105                 110

Ala Gly Lys Ile Met Cys Cys Lys Val Asn Thr Asp Asp Ser Pro Asn
        115                 120                 125

Val Ala Ser Thr Tyr Gly Ile Arg Ser Ile Pro Thr Val Leu Ile Phe
    130                 135                 140

Lys Gly Gly Glu Lys Lys Glu Ser Val Ile Gly Ala Val Pro Lys Ser
```

```
                  145                 150                 155                 160
Thr Leu Thr Thr Leu Ile Asp Lys Tyr Ile Gly Ser Ser Ser
                      165                 170
```

<210> SEQ ID NO 13
<211> LENGTH: 287
<212> TYPE: DNA
<213> ORGANISM: Zea mays
<220> FEATURE:
<221> NAME/KEY: 3'UTR
<222> LOCATION: (1)..(287)
<223> OTHER INFORMATION: ZmCA1 3'UTR

<400> SEQUENCE: 13

```
gttcaaaact agggctacgg caattctacc ggcccgccga ctcctgcatc atcataaata    60
tatatactat actatactac tacgtaccta ccgatatgca cccgagcaat gtgaatgcgt   120
cgagtactat atatctgttt tctgcatcta catatatata ccggatcaat cgcccaatgt   180
gaatgtaata agcaatatca ttttctacca cttttcattc ctaacgctga gcttttatg   240
tactatatct tatgatga ataataatat gaccgccttg tgatcta                   287
```

<210> SEQ ID NO 14
<211> LENGTH: 154
<212> TYPE: PRT
<213> ORGANISM: Sorghum bicolor
<220> FEATURE:
<221> NAME/KEY: MISC_FEATURE
<222> LOCATION: (1)..(154)
<223> OTHER INFORMATION: ferredoxin-thioredoxin reductase

<400> SEQUENCE: 14

```
Met Thr Ser Thr Val Thr Thr Thr Val Gly Cys Gly Gly Leu Pro Val
1               5                   10                  15

Arg Pro Ser Ser Ser Thr Ala Arg Arg Gly Arg Pro Arg Arg Cys
            20                  25                  30

Ala Val Arg Ala Gln Ala Ala Gly Ala Asp Ala Ser Asn Asp Lys Ser
        35                  40                  45

Val Glu Val Met Arg Lys Phe Ser Glu Gln Tyr Ala Arg Arg Ser Asn
    50                  55                  60

Thr Phe Phe Cys Ala Asp Lys Thr Val Thr Ala Val Val Ile Lys Gly
65                  70                  75                  80

Leu Ala Asp His Arg Asp Thr Leu Gly Ala Pro Leu Cys Pro Cys Arg
                85                  90                  95

His Tyr Asp Asp Lys Ala Ala Glu Val Ala Gln Gly Phe Trp Asn Cys
            100                 105                 110

Pro Cys Val Pro Met Arg Glu Arg Lys Glu Cys His Cys Met Leu Phe
        115                 120                 125

Leu Thr Pro Asp Asn Asp Phe Ala Gly Lys Asp Gln Val Ile Ser Leu
    130                 135                 140

Glu Glu Ile Lys Glu Ala Thr Ser Lys Phe
145                 150
```

<210> SEQ ID NO 15
<211> LENGTH: 153
<212> TYPE: PRT
<213> ORGANISM: Setaria italica
<220> FEATURE:
<221> NAME/KEY: MISC_FEATURE
<222> LOCATION: (1)..(153)
<223> OTHER INFORMATION: ferredoxin-thioredoxin reductase

<400> SEQUENCE: 15

Met Thr Ser Ala Val Ala Thr Thr Val Gly Cys Gly Leu Pro Phe
1               5                   10                  15

Arg Pro Ser Ser Ala Ala Pro Arg Gly Arg Pro Arg Gly Arg Trp Met
            20                  25                  30

Val Arg Ala Gln Ala Ala Gly Ala Asp Ala Ser Asp Lys Ser Leu
        35                  40                  45

Glu Ile Met Arg Lys Phe Ser Glu Gln Tyr Ala Arg Arg Ser Asn Thr
    50                  55                  60

Phe Phe Cys Ala Asp Lys Ser Val Thr Ala Val Val Ile Lys Gly Leu
65                  70                  75                  80

Ala Asp His Arg Asp Thr Leu Gly Ala Pro Leu Cys Pro Cys Arg His
            85                  90                  95

Tyr Asp Asp Lys Ala Ala Glu Val Ala Gln Gly Phe Trp Asn Cys Pro
            100                 105                 110

Cys Val Pro Met Arg Glu Arg Lys Glu Cys His Cys Met Leu Phe Leu
            115                 120                 125

Thr Pro Asp Asn Asp Phe Ala Gly Gln Asp Gln Ala Ile Ser Leu Glu
    130                 135                 140

Glu Ile Lys Glu Ala Thr Ser Lys Phe
145                 150

<210> SEQ ID NO 16
<211> LENGTH: 152
<212> TYPE: PRT
<213> ORGANISM: Diplachne fusca
<220> FEATURE:
<221> NAME/KEY: MISC_FEATURE
<222> LOCATION: (1)..(152)
<223> OTHER INFORMATION: ferredoxin-thioredoxin reductase

<400> SEQUENCE: 16

Met Leu Pro Thr Val Ala Ala Thr Val Gly Ser Gly Val Leu Pro Val
1               5                   10                  15

Arg Pro Ser Ser Thr Ala Pro Ser Gly Arg Ser Arg Arg Phe Ala Val
            20                  25                  30

Arg Ala Gln Ala Glu Ala Ala Gly Asp Pro Gly Asp Lys Ser Val Glu
        35                  40                  45

Ile Met Arg Lys Phe Ser Glu Gln Tyr Ala Arg Arg Ser Asn Thr Tyr
    50                  55                  60

Phe Cys Ala Asp Lys Thr Val Thr Ala Val Val Ile Lys Gly Leu Ala
65                  70                  75                  80

Asp His Lys Asp Gln Leu Gly Ala Pro Leu Cys Pro Cys Arg His Tyr
            85                  90                  95

Asp Asp Lys Ala Ala Glu Val Ala Gln Gly Phe Trp Asn Cys Pro Cys
            100                 105                 110

Val Pro Met Arg Glu Arg Lys Glu Cys His Cys Met Leu Phe Leu Thr
            115                 120                 125

Pro Glu Asn Asp Phe Ala Gly Gln Asp Gln Ala Ile Thr Phe Glu Glu
    130                 135                 140

Ile Lys Glu Ala Thr Ser Lys Phe
145                 150

<210> SEQ ID NO 17
<211> LENGTH: 149
<212> TYPE: PRT
<213> ORGANISM: Brachypodium distachyon

```
<220> FEATURE:
<221> NAME/KEY: MISC_FEATURE
<222> LOCATION: (1)..(149)
<223> OTHER INFORMATION: ferredoxin-thioredoxin reductase

<400> SEQUENCE: 17

Met Ser Ser Ser Phe Thr Thr Thr Ala Val Arg Ser Pro Leu Leu Cys
1               5                   10                  15

Pro Ile Ser Thr Ser Ala Ala Gly Leu Arg Arg Arg Ala Val Arg Ala
            20                  25                  30

Gln Ala Gly Gly Val Asp Ser Ser Asp Lys Ser Val Glu Ile Met Arg
        35                  40                  45

Lys Phe Ser Glu Gln Tyr Ala Arg Arg Ser Ser Thr Phe Phe Cys Ser
50                  55                  60

Asp Lys Ser Val Thr Ala Val Val Ile Lys Gly Leu Ala Asp His Lys
65                  70                  75                  80

Asp Gln Leu Gly Ala Pro Leu Cys Pro Cys Arg His Tyr Asp Asp Lys
                85                  90                  95

Ala Ala Glu Ala Ala Gln Gly Phe Trp Asn Cys Pro Cys Val Pro Met
            100                 105                 110

Arg Glu Arg Lys Glu Cys His Cys Met Leu Phe Leu Thr Pro Asp Asn
        115                 120                 125

Asp Phe Ala Gly Glu Asp Gln Ala Ile Ser Leu Asp Glu Ile Lys Glu
130                 135                 140

Ala Thr Ser Lys Phe
145

<210> SEQ ID NO 18
<211> LENGTH: 157
<212> TYPE: PRT
<213> ORGANISM: Aegilops tauschii subsp. tauschii
<220> FEATURE:
<221> NAME/KEY: MISC_FEATURE
<222> LOCATION: (1)..(157)
<223> OTHER INFORMATION: ferredoxin-thioredoxin reductase

<400> SEQUENCE: 18

Met Met Ser Ile Thr Ser Thr Ala Ala Ala Gly Thr Pro Leu Cys Arg
1               5                   10                  15

Pro Ser Val Ser Arg Gly Gly Arg Arg Ser Arg Cys Ala Val Arg Ala
            20                  25                  30

Gln Ala Ala Gly Asp Gly Gly Ala Ala Ala Asp Gly Ala Ser Ser Glu
        35                  40                  45

Gln Lys Ser Leu Glu Ile Met Arg Lys Phe Ser Glu Gln Tyr Ala Arg
50                  55                  60

Arg Ser Ser Thr Phe Phe Cys Ser Asp Lys Ser Val Thr Ala Val Val
65                  70                  75                  80

Ile Lys Gly Leu Ala Asp His Lys Asp Gln Leu Gly Ala Pro Leu Cys
                85                  90                  95

Pro Cys Arg His Tyr Asp Asp Lys Ala Ala Glu Ala Ala Gln Gly Phe
            100                 105                 110

Trp Asn Cys Pro Cys Val Pro Met Arg Glu Arg Lys Glu Cys His Cys
        115                 120                 125

Met Leu Phe Leu Thr Pro Asp Asn Asp Phe Ala Gly Glu Asp Gln Ala
130                 135                 140

Ile Ser Leu Glu Glu Ile Lys Glu Ala Thr Ser Lys Tyr
145                 150                 155
```

```
<210> SEQ ID NO 19
<211> LENGTH: 155
<212> TYPE: PRT
<213> ORGANISM: Oryza brachyantha
<220> FEATURE:
<221> NAME/KEY: MISC_FEATURE
<222> LOCATION: (1)..(155)
<223> OTHER INFORMATION: ferredoxin-thioredoxin reductase

<400> SEQUENCE: 19

Met Met Ser Met Ser Ser Thr Ala Ala Ala Ser Pro Phe Leu Thr Ser
1               5                   10                  15

Pro Met Pro Ser Pro Ser Thr Thr Gly Leu Arg Lys Cys Phe Val
            20                  25                  30

Arg Pro Arg Ala Gln Ala Gly Ser Gly Gly Ala Asp Ala Ser Asp Lys
            35                  40                  45

Ser Ile Glu Ile Met Arg Lys Phe Ser Glu Gln Tyr Ala Arg Arg Ser
    50                  55                  60

Asn Thr Phe Phe Cys Ser Glu Lys Ser Val Thr Ala Val Val Ile Lys
65                  70                  75                  80

Gly Leu Ala Asp His Lys Asp Gln Leu Gly Ala Pro Leu Cys Pro Cys
                85                  90                  95

Arg His Tyr Asp Asp Lys Ala Ala Glu Val Ala Gln Gly Phe Trp Asn
            100                 105                 110

Cys Pro Cys Val Pro Met Arg Glu Arg Lys Glu Cys His Cys Met Leu
        115                 120                 125

Phe Leu Thr Pro Asp Asn Asp Phe Ala Gly Glu Asp Gln Ala Ile Thr
    130                 135                 140

Leu Glu Glu Ile Lys Asp Ala Thr Ser Lys Ile
145                 150                 155

<210> SEQ ID NO 20
<211> LENGTH: 146
<212> TYPE: PRT
<213> ORGANISM: Musa acuminata
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 20

Met Ser Ile Gln Thr Ala Phe Arg Gly Val Ala Leu Pro Ser Leu Thr
1               5                   10                  15

Pro Ala Ser Ser Ser Pro His Arg Pro Pro Arg Phe Met Ile Arg Ala
            20                  25                  30

Glu Val Glu Pro Ser Asp Lys Ser Val Glu Val Met Arg Lys Phe Ser
            35                  40                  45

Glu Gln Tyr Ala Arg Arg Ser Gly Thr Tyr Phe Cys Val Asp Lys Gly
    50                  55                  60

Val Thr Ala Val Val Ile Lys Gly Leu Ala Asp His Arg Asp Ser Val
65                  70                  75                  80

Gly Ala Pro Leu Cys Pro Cys Arg His Tyr Asp Asp Lys Ala Ala Glu
                85                  90                  95

Val Ala Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Thr Glu Gln Ala Ile Ser Phe Glu Glu Ile Lys Glu Thr Thr Ser
```

```
            130             135             140

Lys Ile
145

<210> SEQ ID NO 21
<211> LENGTH: 146
<212> TYPE: PRT
<213> ORGANISM: Oryza sativa
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 21

Met Met Ser Met Ala Ser Thr Thr Ala Ser Pro Phe Cys Pro Ser Pro
1               5                   10                  15

Met Pro Arg Gly Arg Lys Cys Thr Val Arg Val Gln Ala Gly Ala Ala
            20                  25                  30

Gly Ala Asp Ala Ser Asp Lys Ser Leu Glu Ile Met Arg Lys Phe Ser
        35                  40                  45

Glu Gln Tyr Ala Arg Arg Ser Asn Thr Phe Phe Cys Ser Glu Lys Ser
    50                  55                  60

Val Thr Ala Val Val Ile Lys Gly Leu Ala Asp His Lys Asp Gln Leu
65                  70                  75                  80

Gly Ala Pro Leu Cys Pro Cys Arg His Tyr Asp Asp Lys Ala Ala Glu
                85                  90                  95

Val Ala Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Gln Asp Gln Ala Ile Thr Leu Glu Glu Ile Lys Asp Ala Thr Ser
    130                 135                 140

Lys Ile
145

<210> SEQ ID NO 22
<211> LENGTH: 146
<212> TYPE: PRT
<213> ORGANISM: Oryza sativa
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 22

Met Met Leu Met Ala Ser Thr Thr Ala Ser Pro Phe Cys Pro Ser Pro
1               5                   10                  15

Met Pro Arg Gly Arg Lys Cys Thr Val Arg Val Gln Ala Gly Ala Ala
            20                  25                  30

Gly Ala Asp Ala Ser Asp Lys Ser Leu Glu Ile Met Arg Lys Phe Ser
        35                  40                  45

Glu Gln Tyr Ala Arg Arg Ser Asn Thr Phe Phe Cys Ser Glu Lys Ser
    50                  55                  60

Val Thr Ala Val Val Ile Lys Gly Leu Ala Asp His Lys Asp Gln Leu
65                  70                  75                  80

Gly Ala Pro Leu Cys Pro Cys Arg His Tyr Asp Asp Lys Ala Ala Glu
                85                  90                  95

Val Ala Gln Gly Phe Trp Asn Cys Pro Cys Val Pro Met Arg Glu Arg
            100                 105                 110
```

-continued

Lys Glu Cys His Cys Met Leu Phe Leu Thr Pro Asp Asn Asp Phe Ala
            115                 120                 125

Gly Gln Asp Gln Ala Ile Thr Leu Glu Glu Ile Lys Asp Ala Thr Ser
130                 135                 140

Lys Ile
145

<210> SEQ ID NO 23
<211> LENGTH: 201
<212> TYPE: PRT
<213> ORGANISM: Dichanthelium oligosanthes
<220> FEATURE:
<221> NAME/KEY: MISC_FEATURE
<222> LOCATION: (1)..(201)
<223> OTHER INFORMATION: ferredoxin-thioredoxin reductase

<400> SEQUENCE: 23

Met Thr Ser Thr Val Ala Thr Thr Val Gly Cys Gly Gly Leu Pro Phe
1               5                   10                  15

Arg Pro Ser Ser Thr Ala Pro Arg Pro Arg Gly Arg Trp Val Val Arg
            20                  25                  30

Ala Gln Ala Ala Gly Ala Asp Ala Ser Asp Lys Ser Val Glu Ile
        35                  40                  45

Met Arg Lys Phe Ser Glu Gln Tyr Ala Arg Arg Ser Asn Thr Phe Phe
50                  55                  60

Cys Ala Asp Lys Ser Val Thr Ala Val Val Ile Lys Gly Leu Ala Asp
65                  70                  75                  80

His Lys Asp Thr Leu Gly Ala Pro Leu Cys Pro Cys Arg His Tyr Asp
                85                  90                  95

Asp Lys Ala Ala Glu Ala Ala Gln Gly Phe Trp Asn Cys Pro Cys Val
            100                 105                 110

Pro Met Arg Glu Arg Cys Val Cys Gly Leu Tyr Phe Arg Leu Phe Phe
        115                 120                 125

Met Met Val His Arg Glu Asn Val Ala Met Ser Leu Phe Tyr Val Gln
130                 135                 140

Ser Ser Ala Val Leu Leu Gln Tyr Arg Lys His His Phe Leu Cys Glu
145                 150                 155                 160

Trp Ser Thr Phe Ala Gly Lys Asn Ala Thr Val Cys Phe Ser Leu Leu
                165                 170                 175

Gln Thr Met Ile Ser Leu Glu Arg Thr Arg His Val Ile Ser Leu Asp
            180                 185                 190

Glu Ile Lys Glu Ala Thr Ser Lys Phe
        195                 200

<210> SEQ ID NO 24
<211> LENGTH: 147
<212> TYPE: PRT
<213> ORGANISM: Arachis duranensis
<220> FEATURE:
<221> NAME/KEY: MISC_FEATURE
<222> LOCATION: (1)..(147)
<223> OTHER INFORMATION: ferredoxin-thioredoxin reductase

<400> SEQUENCE: 24

Met Thr Ser Gln Ala Ser Ser Ala Ala Ala Phe Ala Leu Pro Val
1               5                   10                  15

Ser Ser Ala Thr Ser Ser Ile Arg Arg Arg Asn Pro Thr Leu Val Arg
            20                  25                  30

-continued

```
Ala Gln Val Glu Pro Ser Asp Lys Ser Val Glu Ile Met Arg Lys Phe
         35                  40                  45

Ser Glu Gln Tyr Ala Arg Arg Ser Gly Thr Tyr Phe Cys Val Asp Lys
 50                  55                  60

Gly Val Thr Ser Val Val Ile Lys Gly Leu Ala Asp His Lys Asp Ser
 65                  70                  75                  80

Leu Gly Ala Pro Leu Cys Pro Cys Arg His Tyr Asp Lys Ala Ala
                 85                  90                  95

Glu Ala Ala Gln Gly Phe Trp Asn Cys Pro Cys Val Pro Met Arg Glu
             100                 105                 110

Arg Lys Glu Cys His Cys Met Leu Phe Leu Thr Pro Asp Asn Asp Phe
             115                 120                 125

Ala Gly Lys Glu Gln Ala Ile Thr Leu Asp Glu Ile Lys Glu Ala Thr
         130                 135                 140

Ala Asn Met
145
```

```
<210> SEQ ID NO 25
<211> LENGTH: 148
<212> TYPE: PRT
<213> ORGANISM: Arachis ipaensis
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 25
```

```
Met Thr Ser His Ala Ser Ser Ala Ala Ala Phe Ala Leu Pro
 1               5                  10                  15

Val Ser Ser Ala Thr Ser Ser Ile Arg Arg Arg Asn Pro Thr Leu Val
             20                  25                  30

Arg Ala Gln Val Glu Pro Ser Asp Lys Ser Val Glu Ile Met Arg Lys
         35                  40                  45

Phe Ser Glu Gln Tyr Ala Arg Arg Ser Gly Thr Tyr Phe Cys Val Asp
 50                  55                  60

Lys Gly Val Thr Ser Val Val Ile Lys Gly Leu Ala Asp His Lys Asp
 65                  70                  75                  80

Ser Leu Gly Ala Pro Leu Cys Pro Cys Arg His Tyr Asp Lys Ala
                 85                  90                  95

Ala Glu Ala Ala Gln Gly Phe Trp Asn Cys Pro Cys Val Pro Met Arg
             100                 105                 110

Glu Arg Lys Glu Cys His Cys Met Leu Phe Leu Thr Pro Asp Asn Asp
             115                 120                 125

Phe Ala Gly Lys Glu Gln Ala Ile Thr Leu Asp Glu Ile Lys Glu Ala
         130                 135                 140

Thr Ala Asn Met
145
```

```
<210> SEQ ID NO 26
<211> LENGTH: 144
<212> TYPE: PRT
<213> ORGANISM: Glycine soja
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 26
```

Met Thr Thr Gln Ala Ser Thr Phe Ala Val Ala Val Pro Ser Val Thr

```
                1               5                   10                  15
            Thr Pro Phe Arg Ser His Arg Asn Pro Phe Val Val Arg Ala Gln Ala
                            20                  25                  30

Glu Pro Ser Asp Lys Ser Val Glu Ile Met Arg Lys Phe Ser Glu Gln
                            35                  40                  45

Tyr Ala Arg Lys Ser Gly Thr Tyr Phe Cys Val Asp Lys Gly Val Thr
                            50                  55                  60

Ser Val Val Ile Lys Gly Leu Ala Asp His Lys Asp Thr Leu Gly Ala
             65                 70                  75                  80

Pro Leu Cys Pro Cys Arg His Tyr Asp Asp Lys Ala Ala Glu Val Ala
                            85                  90                  95

Gln Gly Phe Trp Asn Cys Pro Cys Val Pro Met Arg Glu Arg Lys Glu
                            100                 105                 110

Cys His Cys Met Leu Phe Leu Thr Pro Asp Asn Asp Phe Ala Gly Asn
                            115                 120                 125

Glu Gln Thr Ile Thr Leu Asp Glu Ile Lys Glu Ser Thr Ala Asn Met
                            130                 135                 140

<210> SEQ ID NO 27
<211> LENGTH: 145
<212> TYPE: PRT
<213> ORGANISM: Elaeis guineensis
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 27

Met Ser Thr Gln Thr Ala Leu His Gly Ile Pro Leu Pro Ile Phe Asn
 1               5                   10                  15

Leu Ala Ser Ser Pro Ser Arg Ser His Arg Leu Val Val Arg Ala Lys
                20                  25                  30

Val Glu Pro Ser Glu Lys Ser Val Glu Ile Met Arg Lys Phe Ser Glu
                35                  40                  45

Lys Tyr Ala Arg Gln Ser Gly Thr Tyr Phe Cys Val Asp Lys Gly Val
                50                  55                  60

Thr Ser Val Val Ile Lys Gly Leu Ala Asp His Lys Asp Ser Leu Gly
 65                 70                  75                  80

Ala Pro Leu Cys Pro Cys Arg His Tyr Asp Asp Lys Ala Ala Glu Val
                85                  90                  95

Gly Gln Gly Phe Trp Asn Cys Pro Cys Val Pro Met Arg Glu Arg Lys
                100                 105                 110

Glu Cys His Cys Met Leu Phe Leu Asn Pro Asp Asn Asp Phe Ala Gly
                115                 120                 125

Thr Glu Gln Thr Ile Ser Leu Glu Glu Ile Lys Glu Ala Thr Ser Lys
                130                 135                 140

Ile
145

<210> SEQ ID NO 28
<211> LENGTH: 145
<212> TYPE: PRT
<213> ORGANISM: Eucalyptus grandis
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 28
```

```
Met Thr Leu Gln Ala Ser Ser Phe Ala Ala Val Gly Leu Pro Ser Leu
1               5                   10                  15

Ala Pro Arg Leu Cys Arg Ser Arg Arg Gly Pro Val Val Arg Ala Lys
                20                  25                  30

Val Glu Pro Ser Glu Lys Ser Val Glu Ile Met Arg Lys Phe Ser Glu
            35                  40                  45

Gln Tyr Ala Arg Arg Ser Gly Thr Tyr Phe Cys Val Asp Lys Gly Val
        50                  55                  60

Thr Ser Val Val Ile Lys Gly Leu Ala Asp His Lys Asp Thr Leu Gly
65                  70                  75                  80

Ala Pro Leu Cys Pro Cys Arg His Tyr Asp Asp Lys Pro Ala Glu Val
                85                  90                  95

Ala Gln Gly Phe Trp Asn Cys Pro Cys Val Pro Met Arg Glu Arg Lys
                100                 105                 110

Glu Cys His Cys Met Leu Phe Leu Thr Pro Glu Asn Asp Phe Ala Gly
            115                 120                 125

Gln Asp Gln Ala Ile Ser Phe Glu Glu Ile Lys Glu Ser Thr Ser Asn
        130                 135                 140

Met
145

<210> SEQ ID NO 29
<211> LENGTH: 145
<212> TYPE: PRT
<213> ORGANISM: Vigna radiata
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 29

Met Thr Thr Gln Ala Ser Ala Phe Ser Leu Ala Ala Pro Ser Val Ala
1               5                   10                  15

Thr Pro Phe Arg Gly Arg Asn Arg Asn Pro Leu Leu Val Arg Ala Arg
                20                  25                  30

Val Glu Pro Ser Asp Lys Ser Val Glu Ile Met Arg Lys Phe Ser Glu
            35                  40                  45

Gln Tyr Ala Arg Lys Ser Gly Thr Tyr Phe Cys Val Asp Lys Gly Val
        50                  55                  60

Thr Ser Val Val Ile Lys Gly Leu Ala Asp His Lys Asp Ser Leu Gly
65                  70                  75                  80

Ala Pro Leu Cys Pro Cys Arg His Tyr Asp Asp Lys Ala Ala Glu Ala
                85                  90                  95

Ala Gln Gly Phe Trp Asn Cys Pro Cys Val Pro Met Arg Glu Arg Lys
                100                 105                 110

Glu Cys His Cys Met Leu Phe Leu Thr Pro Asp Asn Asp Phe Ala Gly
            115                 120                 125

Asp Glu Gln Val Ile Thr Leu Glu Glu Ile Lys Glu Ser Thr Ala Asn
        130                 135                 140

Met
145

<210> SEQ ID NO 30
<211> LENGTH: 150
<212> TYPE: PRT
<213> ORGANISM: Musa acuminata
<220> FEATURE:
```

```
<221> NAME/KEY: MISC_FEATURE
<222> LOCATION: (1)..(150)
<223> OTHER INFORMATION: ferredoxin-thioredoxin reductase

<400> SEQUENCE: 30

Met Ala Leu Ser Pro Arg Thr Ala Ala Leu His Gly Val Ala Pro Leu
1               5                   10                  15

Pro Arg Leu Arg Leu Pro Ser Leu Thr Ser Cys Gly Ser Arg Arg Val
            20                  25                  30

Asn Val Arg Ala Lys Val Glu Pro Ser Glu Lys Ser Val Glu Ile Met
        35                  40                  45

Arg Lys Phe Ser Glu Gln Tyr Ala Arg Lys Ser Glu Thr Tyr Phe Cys
50                  55                  60

Ile Asp Lys Gly Val Thr Ser Val Val Ile Lys Gly Leu Ala Asp His
65                  70                  75                  80

Lys Asp Met Leu Gly Ala Pro Leu Cys Pro Cys Arg His Tyr Asp Asp
                85                  90                  95

Lys Ala Ala Glu Val Ala Gln Gly Phe Trp Asn Cys Pro Cys Val Pro
            100                 105                 110

Met Arg Glu Arg Lys Glu Cys His Cys Met Leu Phe Leu Asn Pro Asp
        115                 120                 125

Asn Asp Phe Ala Gly Lys Glu Gln Ser Ile Thr Leu Glu Glu Ile Lys
130                 135                 140

Glu Ala Ile Ser Gln Ile
145                 150

<210> SEQ ID NO 31
<211> LENGTH: 144
<212> TYPE: PRT
<213> ORGANISM: Glycine max
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 31

Met Thr Thr Gln Ala Ser Thr Phe Ala Val Ala Val Pro Ser Val Ala
1               5                   10                  15

Thr Pro Phe Arg Arg His Arg Asn Pro Phe Val Val Arg Ala Gln Ala
            20                  25                  30

Glu Pro Ser Asp Lys Ser Val Glu Ile Met Arg Lys Phe Ser Glu Gln
        35                  40                  45

Tyr Ala Arg Lys Ser Gly Thr Tyr Phe Cys Val Asp Lys Gly Val Thr
50                  55                  60

Ser Val Val Ile Lys Gly Leu Ala Asp His Lys Asp Thr Leu Gly Ala
65                  70                  75                  80

Pro Leu Cys Pro Cys Arg His Tyr Asp Asp Lys Ala Ala Glu Val Ala
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asn
        115                 120                 125

Glu Gln Thr Ile Thr Leu Asp Glu Ile Lys Glu Ser Thr Ala Asn Met
130                 135                 140

<210> SEQ ID NO 32
<211> LENGTH: 145
<212> TYPE: PRT
```

```
<213> ORGANISM: Lupinus angustifolius
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 32

Met Ser Leu Gln Ala Ser Thr Phe Ala Val Ala Ile Pro Phe Ser Thr
1               5                   10                  15

Ala Thr Pro Leu Arg Arg His Arg Asn Leu Phe Thr Val Arg Ala Gln
            20                  25                  30

Val Glu Pro Ser Asp Lys Asn Val Glu Ile Met Arg Lys Phe Ser Glu
        35                  40                  45

Gln Tyr Ala Arg Lys Ser Gly Thr Tyr Phe Cys Val Asp Lys Gly Val
    50                  55                  60

Thr Ser Val Val Ile Lys Gly Leu Ala Asp His Lys Asp Ser Leu Gly
65                  70                  75                  80

Ala Pro Leu Cys Pro Cys Arg His Tyr Asp Asp Lys Ala Ala Glu Ala
                85                  90                  95

Ser Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Glu Gln Thr Ile Thr Leu Glu Glu Ile Lys Glu Ala Thr Ala Asn
    130                 135                 140

Met
145

<210> SEQ ID NO 33
<211> LENGTH: 147
<212> TYPE: PRT
<213> ORGANISM: Ananas comosus
<220> FEATURE:
<221> NAME/KEY: MISC_FEATURE
<222> LOCATION: (1)..(147)
<223> OTHER INFORMATION: ferredoxin-thioredoxin reductase

<400> SEQUENCE: 33

Met Ser Ser Gln Thr Leu Leu Leu Gly Ala Ala Phe Pro Ser Pro Ala
1               5                   10                  15

Leu Ala Leu Ala Pro Ser Arg Ser Arg Ser Arg Leu Arg Ile Arg
            20                  25                  30

Ala Gln Val Glu Pro Ser Asp Lys Ser Val Glu Ile Met Arg Lys Phe
        35                  40                  45

Ser Glu Gln Tyr Ala Arg Lys Ser Gly Thr Tyr Phe Cys Met Asp Lys
    50                  55                  60

Gly Val Thr Ala Val Val Ile Lys Gly Leu Ala Glu His Lys Asp Ser
65                  70                  75                  80

Ile Gly Ala Pro Leu Cys Pro Cys Arg His Tyr Asp Asp Lys Ala Ala
                85                  90                  95

Glu Val Gly Gln Gly Phe Trp Asn Cys Pro Cys Val Pro Met Arg Glu
            100                 105                 110

Arg Lys Glu Cys His Cys Met Leu Phe Leu Thr Pro Glu Asn Asp Phe
        115                 120                 125

Ala Gly Lys Glu Gln Ala Ile Thr Leu Glu Glu Ile Lys Glu Ala Thr
    130                 135                 140

Ser Lys Leu
145
```

-continued

```
<210> SEQ ID NO 34
<211> LENGTH: 145
<212> TYPE: PRT
<213> ORGANISM: Tarenaya hassleriana
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 34

Met Asn Leu Gln Ala Ala Ser Cys Ser Phe Ser Ser Val Trp Val Pro
1               5                   10                  15

Leu Ala Ser Pro Arg Thr Ser Ser Arg Arg Ser Val Ile Arg Ala Lys
            20                  25                  30

Ser Glu Pro Ser Glu Lys Ser Val Glu Ile Met Arg Lys Phe Ser Glu
        35                  40                  45

Gln Tyr Ala Arg Arg Ser Gly Thr Tyr Phe Cys Val Asp Lys Gly Val
    50                  55                  60

Thr Ala Val Val Ile Lys Gly Leu Ala Glu His Lys Asp Ser His Gly
65                  70                  75                  80

Ala Pro Leu Cys Pro Cys Arg His Tyr Asp Asp Lys Ala Ala Glu Val
                85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Lys Asp Gln Ala Ile Ser Leu Glu Glu Ile Asn Glu Ala Thr Ala Asn
    130                 135                 140

Met
145

<210> SEQ ID NO 35
<211> LENGTH: 146
<212> TYPE: PRT
<213> ORGANISM: Phoenix dactylifera
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 35

Met Ser Thr Gln Thr Ala Ala Phe His Gly Val Pro Leu Pro Ile Phe
1               5                   10                  15

Gln Pro Ala Ser Pro His Pro Arg Pro Arg Arg Leu Leu Val Arg Ala
            20                  25                  30

Lys Val Glu Pro Ser Glu Lys Ser Val Glu Leu Met Arg Arg Phe Ser
        35                  40                  45

Glu Lys Tyr Ala Arg Gln Ser Gly Thr Tyr Phe Cys Val Asp Lys Gly
    50                  55                  60

Val Thr Ser Val Val Ile Lys Gly Leu Ala Asp His Lys Asp Ser His
65                  70                  75                  80

Gly Ala Pro Leu Cys Pro Cys Arg His Tyr Asp Asp Lys Ser Ala Glu
                85                  90                  95

Val Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125
```

```
Gly Lys Glu Gln Ala Ile Thr Leu Glu Glu Ile Lys Glu Ala Thr Ser
            130                 135                 140

His Val
145

<210> SEQ ID NO 36
<211> LENGTH: 149
<212> TYPE: PRT
<213> ORGANISM: Selaginella moellendorffii
<220> FEATURE:
<221> NAME/KEY: MISC_FEATURE
<222> LOCATION: (1)..(149)
<223> OTHER INFORMATION: ferredoxin-thioredoxin reductase

<400> SEQUENCE: 36

Met Ala Ala Met Ala Ser Ile Ala Thr Thr Ser Arg Asn Leu Gly Gly
1               5                   10                  15

Ala Phe Val Asn Pro Ser Ser Thr Pro Arg Arg Ile His Val Val
                20                  25                  30

Arg Ala Ser Ser Glu Pro Ser Ser Lys Ser Ile Glu Asn Met Arg Lys
            35                  40                  45

Phe Ser Glu Gln Tyr Ala Arg Arg Ser Gly Thr Tyr Phe Cys Ala Asp
    50                  55                  60

Lys Ser Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Pro
                85                  90                  95

Ala Glu Ala Ser Gln Gly Phe Trp Asn Cys Pro Cys Val Pro Met Arg
            100                 105                 110

Glu Arg Lys Glu Cys His Cys Met Leu Phe Leu Thr Pro Glu Asn Asp
        115                 120                 125

Phe Ala Gly Lys Asp Gln Thr Ile Ser Ala Asp Glu Ile Lys Asp Leu
    130                 135                 140

Thr Ala Ser Leu Gly
145

<210> SEQ ID NO 37
<211> LENGTH: 154
<212> TYPE: PRT
<213> ORGANISM: Lupinus angustifolius
<220> FEATURE:
<221> NAME/KEY: MISC_FEATURE
<222> LOCATION: (1)..(154)
<223> OTHER INFORMATION: ferredoxin-thioredoxin reductase

<400> SEQUENCE: 37

Met Ser Leu Gln Ala Ser Thr Phe Ala Val Ala Ile Pro Phe Ser Thr
1               5                   10                  15

Ala Thr Pro Leu Arg Arg His Arg Asn Leu Phe Thr Val Arg Ala Gln
                20                  25                  30

Asp Gly Asn Asn Leu Leu Val Leu Ala Val Glu Pro Ser Asp Lys Asn
            35                  40                  45

Val Glu Ile Met Arg Lys Phe Ser Glu Gln Tyr Ala Arg Lys Ser Gly
    50                  55                  60

Thr Tyr Phe Cys Val Asp Lys Gly Val Thr Ser Val Val Ile Lys Gly
65                  70                  75                  80

Leu Ala Asp His Lys Asp Ser Leu Gly Ala Pro Leu Cys Pro Cys Arg
                85                  90                  95

His Tyr Asp Asp Lys Ala Ala Glu Ala Ser Gln Gly Phe Trp Asn Cys
```

```
                100             105             110
Pro Cys Val Pro Met Arg Glu Arg Lys Glu Cys His Cys Met Leu Phe
            115                 120                 125

Leu Thr Pro Asp Asn Asp Phe Ala Gly Gln Glu Gln Thr Ile Thr Leu
            130                 135                 140

Glu Glu Ile Lys Glu Ala Thr Ala Asn Met
145                 150

<210> SEQ ID NO 38
<211> LENGTH: 140
<212> TYPE: PRT
<213> ORGANISM: Glycine max
<220> FEATURE:
<221> NAME/KEY: MISC_FEATURE
<222> LOCATION: (1)..(140)
<223> OTHER INFORMATION: ferredoxin-thioredoxin reductase

<400> SEQUENCE: 38

Met Thr Thr Gln Ala Ser Thr Phe Ala Val Ala Val Pro Ser Val Thr
1               5                   10                  15

Thr Pro Phe Arg Ser His Arg Asn Pro Phe Val Val Arg Ala Gln Asp
            20                  25                  30

Lys Ser Val Glu Ile Met Arg Lys Phe Ser Glu Gln Tyr Ala Arg Lys
        35                  40                  45

Ser Gly Thr Tyr Phe Cys Val Asp Lys Gly Val Thr Ser Val Val Ile
    50                  55                  60

Lys Gly Leu Ala Asp His Lys Asp Thr Leu Gly Ala Pro Leu Cys Pro
65                  70                  75                  80

Cys Arg His Tyr Asp Asp Lys Ala Ala Glu Val Ala Gln Gly Phe Trp
                85                  90                  95

Asn Cys Pro Cys Val Pro Met Arg Glu Arg Lys Glu Cys His Cys Met
            100                 105                 110

Leu Phe Leu Thr Pro Asp Asn Asp Phe Ala Gly Asn Glu Gln Thr Ile
        115                 120                 125

Thr Leu Asp Glu Ile Lys Glu Ser Thr Ala Asn Met
    130                 135                 140

<210> SEQ ID NO 39
<211> LENGTH: 149
<212> TYPE: PRT
<213> ORGANISM: Populus euphratica
<220> FEATURE:
<221> NAME/KEY: MISC_FEATURE
<222> LOCATION: (1)..(149)
<223> OTHER INFORMATION: ferredoxin-thioredoxin reductase

<400> SEQUENCE: 39

Met Asn Trp Ser Cys Ser Thr Ala Thr Thr Cys Gly Ile Ser Ser Ser
1               5                   10                  15

Ser Ser Cys Phe Ser Cys Pro Pro Lys Thr Pro Phe Arg Ala Val Ile
            20                  25                  30

Arg Ala Ser Lys Val Glu Pro Ser Asp Lys Ser Val Glu Ile Met Arg
        35                  40                  45

Lys Phe Ser Glu Gln Tyr Ala Arg Lys Ser Gly Thr Tyr Phe Cys Val
    50                  55                  60

Asp Lys Gly Val Thr Ser Val Val Ile Lys Gly Leu Ala Asp His Lys
65                  70                  75                  80

Asp Ser Leu Gly Ala Pro Leu Cys Pro Cys Arg His Tyr Asp Asp Lys
                85                  90                  95
```

```
Ala Ala Glu Ala Gly Gln Gly Phe Trp Asn Cys Pro Cys Val Pro Met
            100                 105                 110

Arg Glu Arg Lys Glu Cys His Cys Met Leu Phe Leu Thr Pro Asp Asn
        115                 120                 125

Asp Phe Ala Gly Lys Asp Gln Thr Ile Ser Leu Glu Glu Ile Arg Glu
    130                 135                 140

Ser Thr Ala Asn Met
145

<210> SEQ ID NO 40
<211> LENGTH: 148
<212> TYPE: PRT
<213> ORGANISM: Nicotiana tabacum
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 40

Met Thr Thr Leu Gln Ala Ser Thr Ser Tyr Ser Val Gly Phe Gly Ile
1               5                   10                  15

Ser Ser Phe Ala Thr Leu Pro Lys Ser Ser Arg Arg Tyr Val Thr
            20                  25                  30

Val Ala Lys Met Glu Pro Ser Glu Lys Ser Val Glu Ile Met Arg Lys
        35                  40                  45

Phe Ser Glu Gln Tyr Ala Arg Arg Ser Gly Thr Tyr Phe Cys Met Asp
    50                  55                  60

Lys Gly Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
        115                 120                 125

Phe Ala Gly Glu Glu Gln Ala Ile Ser Met Glu Glu Ile Lys Glu Thr
    130                 135                 140

Thr Ala Asn Met
145

<210> SEQ ID NO 41
<211> LENGTH: 144
<212> TYPE: PRT
<213> ORGANISM: Cicer arietinum
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 41

Met Thr Thr Gln Ala Ser Thr Phe Ala Phe Ser Val Ser Ser Val Ala
1               5                   10                  15

Ser Pro Leu Arg Arg Arg Arg Asn Pro Thr Val Val Arg Ala Gln Val
            20                  25                  30

Glu Pro Ser Asp Lys Ser Val Glu Ile Met Arg Lys Phe Ser Glu Gln
        35                  40                  45

Tyr Ala Arg Lys Ser Glu Thr Phe Phe Cys Val Asp Lys Gly Val Thr
    50                  55                  60
```

```
Ser Val Val Ile Lys Gly Leu Ala Asp His Lys Asp Ser Leu Gly Ala
 65                  70                  75                  80

Pro Leu Cys Pro Cys Arg His Tyr Asp Asp Lys Ala Ala Glu Ala Ala
             85                  90                  95

His Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asn
        115                 120                 125

Glu Gln Thr Ile Thr Leu Asp Glu Ile Lys Glu Ser Thr Ala Asn Met
    130                 135                 140
```

<210> SEQ ID NO 42
<211> LENGTH: 150
<212> TYPE: PRT
<213> ORGANISM: Picea sitchensis
<220> FEATURE:
<221> NAME/KEY: MISC_FEATURE
<222> LOCATION: (1)..(150)
<223> OTHER INFORMATION: ferredoxin-thioredoxin reductase

<400> SEQUENCE: 42

```
Met Ala Thr Ser Val Ile Asn Thr Ser Ile Ser Asn Leu Gly Val Ser
  1               5                  10                  15

Ser Leu Lys Ser Ser Ala Asn Ala Arg Ile Glu Ser Lys Tyr Ser Met
             20                  25                  30

Gln Val Arg Ala Lys Val Glu Pro Ser Asn Lys Ser Val Glu Ile Met
         35                  40                  45

Arg Lys Phe Ser Glu Gln Tyr Ala Arg Arg Ser Asp Thr Tyr Phe Cys
 50                  55                  60

Val Asp Lys Ala Val Thr Ser Val Val Ile Lys Gly Leu Ala Glu His
 65                  70                  75                  80

Lys Asp Thr Leu Gly Ala Pro Leu Cys Pro Cys Arg His Tyr Asp Asp
             85                  90                  95

Lys Val Ala Glu Ala Glu Gln Gly Phe Trp Asn Cys Pro Cys Val Pro
        100                 105                 110

Met Arg Glu Arg Lys Glu Cys His Cys Met Leu Phe Leu Thr Thr Asp
    115                 120                 125

Asn Asp Phe Ser Gly Lys Glu Gln Thr Ile Ser Glu Glu Ile Lys
130                 135                 140

Asp Leu Thr Ala Lys Phe
145                 150
```

<210> SEQ ID NO 43
<211> LENGTH: 144
<212> TYPE: PRT
<213> ORGANISM: Trifolium subterraneum
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 43

```
Met Thr Ser Gln Ala Ser Thr Phe Ala Val Ser Val Ser Ser Val Ala
  1               5                  10                  15

Ser Pro Leu Arg Arg Arg Asn Phe His Val Val Arg Ala Gln Val
             20                  25                  30

Glu Pro Ser Asp Lys Ser Ile Glu Ile Met Arg Lys Phe Ser Glu Gln
         35                  40                  45

Tyr Ala Arg Lys Ser Gly Thr Tyr Phe Cys Ser Asp Lys Gly Val Thr
```

```
                    50                  55                  60

Ala Val Val Ile Lys Gly Leu Ala Asp His Lys Asp Ser Leu Gly Ala
 65                  70                  75                  80

Pro Leu Cys Pro Cys Arg His Tyr Asp Asp Lys Ala Ala Glu Ala Ala
                     85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asn
        115                 120                 125

Glu Gln Thr Ile Thr Leu Asp Glu Ile Lys Glu Ser Thr Glu Asn Met
    130                 135                 140
```

<210> SEQ ID NO 44
<211> LENGTH: 153
<212> TYPE: PRT
<213> ORGANISM: Helianthus annuus
<220> FEATURE:
<221> NAME/KEY: MISC_FEATURE
<222> LOCATION: (1)..(153)
<223> OTHER INFORMATION: ferredoxin-thioredoxin reductase

<400> SEQUENCE: 44

```
Met Thr Leu Met Arg Thr Leu Pro Ala Thr Thr Ser Tyr Ala Val Gly
 1               5                  10                  15

Phe Gly Val Ser Ser Phe Asn Ala Pro Pro Ser His Leu Arg Tyr Arg
                20                  25                  30

Arg Phe Val Ile Ala Asn Ala Ser Ala Glu Pro Ser Asp Lys Ser Val
            35                  40                  45

Glu Ile Met Arg Lys Phe Ser Glu Gln Tyr Ala Arg Arg Ser Gly Thr
    50                  55                  60

Tyr Phe Cys Val Asp Lys Ser Val Thr Ser Val Val Ile Lys Gly Leu
 65                  70                  75                  80

Ala Asp His Lys Asp Ser Leu Gly Ala Pro Leu Cys Pro Cys Arg His
                85                  90                  95

Tyr Asp Asp Lys Ala Ala Glu Ala Thr Gln Gly Phe Trp Asn Cys Pro
            100                 105                 110

Cys Val Pro Met Arg Glu Arg Lys Glu Cys His Cys Met Leu Phe Leu
        115                 120                 125

Thr Pro Asp Asn Asp Phe Ala Gly Asn Glu Gln Val Ile Thr Met Glu
    130                 135                 140

Glu Ile Lys Glu Ser Thr Ala Asn Met
145                 150
```

<210> SEQ ID NO 45
<211> LENGTH: 144
<212> TYPE: PRT
<213> ORGANISM: Cucumis melo
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 45

```
Met Ile Leu Gln Ala Ser Ser Phe Asn Ile Ala Val Pro Leu Ser Gly
 1               5                  10                  15

Ser Ser Leu Gly Cys Ser Arg His Arg His Val Val Arg Ala Gln Ala
                20                  25                  30

Glu Pro Ser Glu Lys Ser Val Glu Ile Met Arg Lys Phe Ser Glu Gln
            35                  40                  45
```

```
Tyr Ala Arg Lys Ser Gly Thr Tyr Phe Cys Val Asp Lys Gly Val Thr
        50                  55                  60

Ala Val Val Ile Lys Gly Leu Ala Asp His Lys Asp Thr Leu Gly Ala
 65                  70                  75                  80

Pro Leu Cys Pro Cys Arg His Tyr Asp Asp Lys Pro Ala Glu Val Ala
                85                  90                  95

Gln Gly Phe Trp Asn Cys Pro Cys Val Pro Met Arg Glu Arg Lys Glu
               100                 105                 110

Cys His Cys Met Leu Phe Leu Thr Pro Glu Asn Asp Phe Ala Gly Asn
               115                 120                 125

Asp Gln Ala Ile Ser Leu Glu Asp Ile Arg Ala Thr Thr Ala Asn Met
               130                 135                 140

<210> SEQ ID NO 46
<211> LENGTH: 148
<212> TYPE: PRT
<213> ORGANISM: Capsicum annuum
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 46

Met Gly Thr Leu Gln Ala Ser Thr Ser Tyr Ser Ile Gly Phe Gly Ile
 1               5                  10                  15

Ser Ser Leu Ala Ala Leu Pro Lys Pro Ser Thr Arg Arg Cys Leu Thr
                20                  25                  30

Val Ala Lys Met Glu Pro Ser Glu Lys Ser Val Glu Val Met Arg Lys
            35                  40                  45

Phe Ser Glu Gln Tyr Ala Arg Arg Ser Gly Thr Tyr Phe Cys Met Asp
 50                  55                  60

Lys Gly Val Thr Ser Val Val Ile Lys Gly Leu Ala Glu His Lys Asp
 65                  70                  75                  80

Thr Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
        115                 120                 125

Phe Ala Gly Glu Glu Thr Ile Ser Met Glu Glu Ile Lys Glu Thr
    130                 135                 140

Thr Ala Asn Met
145

<210> SEQ ID NO 47
<211> LENGTH: 145
<212> TYPE: PRT
<213> ORGANISM: Sesamum indicum
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 47

Met Arg Ala Leu Gln Ala Ser Thr Ser Tyr Ser Val Ser Phe Ala Ile
 1               5                  10                  15

Pro Ser Val Ala Arg Pro Pro Arg Arg His Gly Ile Val Ala Lys
                20                  25                  30
```

```
Val Glu Pro Thr Glu Lys Ser Val Glu Ile Met Arg Lys Phe Ser Glu
         35                  40                  45

Gln Tyr Ala Arg Lys Ser Gly Thr Tyr Phe Cys Val Asp Lys Gly Val
     50                  55                  60

Thr Ser Val Val Ile Lys Gly Leu Ala Glu His Lys Asp Thr Leu Gly
 65                  70                  75                  80

Ala Pro Leu Cys Pro Cys Arg His Tyr Asp Asp Lys Ala Ala Glu Ala
                 85                  90                  95

Gln Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Glu Gln Val Ile Ser Leu Glu Glu Ile Lys Glu Thr Thr Ala Asn
    130                 135                 140

Met
145

<210> SEQ ID NO 48
<211> LENGTH: 148
<212> TYPE: PRT
<213> ORGANISM: Citrus clementina
<220> FEATURE:
<221> NAME/KEY: MISC_FEATURE
<222> LOCATION: (1)..(148)

<400> SEQUENCE: 48

Met Thr Leu Gln Ser Ser Leu Cys Gly Ser Gly Val Ser Thr Phe Ile
 1               5                  10                  15

Cys Thr Pro Arg Pro Ile Ile Ala Arg Ser Arg Pro Val Thr Gln Ile
                 20                  25                  30

Arg Ala Gln Val Glu Pro Ser Gly Lys Ser Val Glu Ile Met Arg Lys
             35                  40                  45

Phe Ser Glu Gln Tyr Ala Arg Arg Ser Asp Thr Phe Phe Cys Val Asp
     50                  55                  60

Lys Ser Val Thr Ser Val Val Ile Lys Gly Leu Ala Asp His Lys Asp
 65                  70                  75                  80

Ser Leu Gly Ala Pro Leu Cys Pro Cys Arg His Tyr Asp Asp Lys Ala
                 85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Glu Asn Asp
        115                 120                 125

Phe Ala Gly Gln Asp Gln Ser Ile Ser Leu Asp Glu Ile Lys Glu Ser
    130                 135                 140

Thr Ala Asn Met
145

<210> SEQ ID NO 49
<211> LENGTH: 144
<212> TYPE: PRT
<213> ORGANISM: Phaseolus vulgaris
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 49

Met Thr Thr Gln Ala Ser Ala Phe Ser Leu Gly Val Pro Ser Val Ala
 1               5                  10                  15
```

Thr Pro Phe Arg Arg His Arg Asn Pro Val Thr Val Arg Ala Arg Ala
            20                  25                  30

Glu Pro Ser Asp Lys Ser Val Asp Ile Met Arg Lys Phe Ser Glu Gln
        35                  40                  45

Tyr Ala Arg Lys Ser Gly Thr Tyr Phe Cys Ala Asp Lys Gly Val Thr
    50                  55                  60

Ala Val Val Ile Lys Gly Leu Ala Asp His Lys Asp Ser Leu Gly Ala
65                  70                  75                  80

Pro Leu Cys Pro Cys Arg His Tyr Asp Asp Lys Ala Ala Glu Ala Ala
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asp
        115                 120                 125

Glu Gln Ala Ile Thr Leu Asp Glu Ile Lys Glu Ser Thr Ala Asn Met
    130                 135                 140

<210> SEQ ID NO 50
<211> LENGTH: 144
<212> TYPE: PRT
<213> ORGANISM: Sesamum indicum
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 50

Met Arg Ala Leu Gln Ala Ser Thr Ser Tyr Ser Val Ser Phe Ala Ile
1               5                   10                  15

Pro Ser Val Ala Arg Pro Pro Arg Arg His Gly Ile Val Ala Lys
            20                  25                  30

Glu Pro Thr Glu Lys Ser Val Glu Ile Met Arg Lys Phe Ser Glu Gln
        35                  40                  45

Tyr Ala Arg Lys Ser Gly Thr Tyr Phe Cys Val Asp Lys Gly Val Thr
    50                  55                  60

Ser Val Val Ile Lys Gly Leu Ala Glu His Lys Asp Thr Leu Gly Ala
65                  70                  75                  80

Pro Leu Cys Pro Cys Arg His Tyr Asp Asp Lys Ala Ala Glu Ala Gln
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Gln
        115                 120                 125

Glu Gln Val Ile Ser Leu Glu Glu Ile Lys Glu Thr Thr Ala Asn Met
    130                 135                 140

<210> SEQ ID NO 51
<211> LENGTH: 146
<212> TYPE: PRT
<213> ORGANISM: Arabidopsis lyrata
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 51

Met Asn Leu Gln Ala Val Ser Cys Ser Phe Gly Phe Val Ser Ser Pro
1               5                   10                  15

Leu Gly Val Thr Pro Arg Thr Ser Phe Arg Arg Phe Val Ile Arg Ala
            20                  25                  30

Lys Thr Glu Pro Ser Glu Lys Ser Val Glu Ile Met Arg Lys Phe Ser
        35                  40                  45

Glu Gln Tyr Ala Arg Arg Ser Gly Thr Tyr Phe Cys Val Asp Lys Gly
    50                  55                  60

Val Thr Ser Val Val Ile Lys Gly Leu Ala Glu His Lys Asp Ser Tyr
65                  70                  75                  80

Gly Ala Pro Leu Cys Pro Cys Arg His Tyr Asp Asp Lys Ala Ala Glu
                85                  90                  95

Val Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Lys Asp Gln Thr Ile Thr Ser Asp Glu Ile Lys Glu Thr Thr Ala
    130                 135                 140

Asn Met
145

<210> SEQ ID NO 52
<211> LENGTH: 146
<212> TYPE: PRT
<213> ORGANISM: Arabidopsis thaliana
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 52

Met Asn Leu Gln Ala Val Ser Cys Ser Phe Gly Phe Leu Ser Ser Pro
1               5                   10                  15

Leu Gly Val Thr Pro Arg Thr Ser Phe Arg Arg Phe Val Ile Arg Ala
            20                  25                  30

Lys Thr Glu Pro Ser Glu Lys Ser Val Glu Ile Met Arg Lys Phe Ser
        35                  40                  45

Glu Gln Tyr Ala Arg Arg Ser Gly Thr Tyr Phe Cys Val Asp Lys Gly
    50                  55                  60

Val Thr Ser Val Val Ile Lys Gly Leu Ala Glu His Lys Asp Ser Tyr
65                  70                  75                  80

Gly Ala Pro Leu Cys Pro Cys Arg His Tyr Asp Asp Lys Ala Ala Glu
                85                  90                  95

Val Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Lys Asp Gln Thr Ile Thr Ser Asp Glu Ile Lys Glu Thr Thr Ala
    130                 135                 140

Asn Met
145

<210> SEQ ID NO 53
<211> LENGTH: 146
<212> TYPE: PRT
<213> ORGANISM: Ziziphus jujuba
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 53

Met Ser Ile Gln Ala Thr Cys Ser Ser Phe Gly Val Gly Ile Ser Ser
1               5                   10                  15

Phe Val Ser Pro Leu Thr Arg Ser Arg His Arg Thr Leu Ile Arg Ala
            20                  25                  30

Gln Val Gln Pro Ser Glu Lys Ser Val Glu Ile Met Arg Lys Phe Ser
        35                  40                  45

Glu Gln Tyr Ala Arg Lys Ser Gly Thr Tyr Phe Cys Val Asp Lys Gly
    50                  55                  60

Val Thr Ser Val Val Ile Lys Gly Leu Ala Glu His Lys Asp Thr Leu
65                  70                  75                  80

Gly Ala Pro Leu Cys Pro Cys Arg His Tyr Asp Asp Lys Pro Ala Glu
                85                  90                  95

Ala Gly Gln Gly Phe Trp Asn Cys Pro Cys Val Pro Met Arg Glu Arg
            100                 105                 110

Lys Glu Cys His Cys Met Leu Phe Leu Thr Pro Glu Asn Asp Phe Ala
        115                 120                 125

Gly Lys Glu Gln Thr Ile Ser Phe Asp Glu Ile Lys Glu Ala Thr Ala
    130                 135                 140

Asn Met
145

<210> SEQ ID NO 54
<211> LENGTH: 148
<212> TYPE: PRT
<213> ORGANISM: Citrus sinensis
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 54

Met Thr Leu Gln Ser Ser Leu Cys Gly Ser Gly Val Ser Thr Phe Ile
1               5                   10                  15

Cys Thr Pro Arg Pro Ile Ile Ala Arg Pro Arg Pro Val Thr Gln Ile
            20                  25                  30

Arg Ala Gln Val Glu Pro Ser Glu Lys Ser Val Glu Ile Met Arg Lys
        35                  40                  45

Phe Ser Glu Gln Tyr Ala Arg Arg Ser Asp Thr Phe Phe Cys Val Asp
    50                  55                  60

Lys Ser Val Thr Ser Val Val Ile Lys Gly Leu Ala Asp His Lys Asp
65                  70                  75                  80

Ser Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Glu Asn Asp
        115                 120                 125

Phe Ala Gly Gln Asp Gln Ser Ile Ser Leu Asp Glu Ile Lys Glu Ser
    130                 135                 140

Thr Ala Asn Leu
145

<210> SEQ ID NO 55
<211> LENGTH: 145
<212> TYPE: PRT
<213> ORGANISM: Vitis vinifera

```
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 55

Met Ser Leu Gln Ala Ser Ser Tyr Ala Phe Gly Ile Ser Ser Phe
1               5                   10                  15

Val Ser Pro Arg Arg Val Arg His Val Pro Glu Ile Arg Ala Lys
                20                  25                  30

Val Glu Pro Ser Asp Lys Ser Val Glu Ile Met Arg Lys Phe Ser Glu
                35                  40                  45

Gln Tyr Ala Arg Lys Ser Gly Thr Tyr Phe Cys Val Asp Lys Gly Val
    50                  55                  60

Thr Ser Val Val Ile Lys Gly Leu Ala Asp His Lys Asp Ser Leu Gly
65                  70                  75                  80

Ala Pro Leu Cys Pro Cys Arg His Tyr Asp Asp Lys Ala Ala Glu Ala
                85                  90                  95

Gly Gln Gly Phe Trp Asn Cys Pro Cys Val Pro Met Arg Glu Arg Lys
                100                 105                 110

Glu Cys His Cys Met Leu Phe Leu Thr Pro Asp Asn Asp Phe Ala Gly
                115                 120                 125

Gln Asp Gln Thr Ile Ser Leu Glu Glu Ile Arg Glu Ser Thr Ala Asn
    130                 135                 140

Met
145

<210> SEQ ID NO 56
<211> LENGTH: 146
<212> TYPE: PRT
<213> ORGANISM: Malus domestica
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 56

Met Thr Leu Gln Leu Gln Ala Pro Ser Phe Ala Ala Gly Ile Ser Ser
1               5                   10                  15

Phe Val Ser Pro Leu Asn Arg Ser Thr Arg Arg Pro Val Ile Arg Ala
                20                  25                  30

Lys Ala Glu Pro Ser Asp Lys Ser Val Glu Ile Met Arg Lys Phe Ser
                35                  40                  45

Glu Gln Tyr Ala Arg Lys Ser Gly Thr Tyr Phe Cys Val Asp Lys Gly
    50                  55                  60

Val Thr Ser Val Val Ile Lys Gly Leu Ala Asp His Lys Asp Ser Leu
65                  70                  75                  80

Gly Ala Pro Leu Cys Pro Cys Arg His Tyr Asp Asp Lys Pro Ala Glu
                85                  90                  95

Ala Gly Gln Gly Phe Trp Asn Cys Pro Cys Val Pro Met Arg Glu Arg
                100                 105                 110

Lys Glu Cys His Cys Met Leu Phe Leu Thr Pro Asp Asn Asp Phe Ala
                115                 120                 125

Gly Pro Glu Gln Thr Ile Ser Leu Glu Glu Ile Arg Glu Ser Thr Ala
    130                 135                 140

Asn Met
145
```

<210> SEQ ID NO 57
<211> LENGTH: 146
<212> TYPE: PRT
<213> ORGANISM: Camelina sativa
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 57

Met Asn Leu Gln Ala Ala Ser Cys Ser Phe Gly Phe Val Ser Ser Pro
1               5                   10                  15

Leu Gly Val Thr Pro Gly Thr Ser Phe Arg Arg Phe Val Ile Arg Ala
            20                  25                  30

Lys Ser Glu Pro Ser Glu Lys Ser Val Glu Ile Met Arg Lys Phe Ser
        35                  40                  45

Glu Gln Tyr Ala Arg Arg Ser Gly Thr Tyr Phe Cys Val Asp Lys Gly
    50                  55                  60

Val Thr Ser Val Val Ile Lys Gly Leu Ala Glu His Lys Asp Ser Tyr
65                  70                  75                  80

Gly Ala Pro Leu Cys Pro Cys Arg His Tyr Asp Asp Lys Ala Ala Glu
                85                  90                  95

Val Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Lys Asp Gln Thr Ile Thr Ser Glu Glu Ile Lys Glu Thr Thr Ala
    130                 135                 140

Asn Met
145

<210> SEQ ID NO 58
<211> LENGTH: 150
<212> TYPE: PRT
<213> ORGANISM: Asparagus officinalis
<220> FEATURE:
<221> NAME/KEY: MISC_FEATURE
<222> LOCATION: (1)..(150)
<223> OTHER INFORMATION: ferredoxin-thioredoxin reductase

<400> SEQUENCE: 58

Met Ser Ile Gln Ala Gln Ala Ser Ala Gly Val Gly Ala Phe Val Gly
1               5                   10                  15

Val Gly Pro Arg Leu Pro Pro Pro Ser Ile Arg Arg Ser Arg Arg
            20                  25                  30

Val Val Arg Ala Lys Ala Glu Pro Ser Glu Lys Ser Val Glu Ile Met
            35                  40                  45

Arg Lys Phe Ser Glu Gln Tyr Ala Arg Arg Ser Gly Thr Tyr Phe Cys
    50                  55                  60

Val Asp Lys Gly Val Thr Ser Val Val Ile Lys Gly Leu Ala Asp His
65                  70                  75                  80

Lys Asp Ser Leu Gly Ala Pro Leu Cys Pro Cys Arg His Tyr Asp Asp
                85                  90                  95

Lys Ala Ala Glu Ala Gly Gln Gly Phe Trp Asn Cys Pro Cys Val Pro
            100                 105                 110

Met Arg Glu Arg Lys Glu Cys His Cys Met Leu Phe Leu Thr Pro Asp
        115                 120                 125

Asn Asp Phe Ala Gly Ala Asp Gln Thr Ile Thr Leu Glu Glu Ile Lys

Glu Ser Thr Ser Ser Leu
145                 150

<210> SEQ ID NO 59
<211> LENGTH: 148
<212> TYPE: PRT
<213> ORGANISM: Citrus sinensis
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 59

Met Thr Leu Gln Ser Ser Leu Cys Gly Ser Gly Val Ser Thr Phe Ile
1               5                   10                  15

Cys Thr Pro Arg Pro Ile Ile Ala Arg Pro Arg Pro Val Thr Gln Ile
            20                  25                  30

Arg Ala Gln Val Glu Pro Ser Glu Lys Ser Val Glu Ile Met Arg Lys
        35                  40                  45

Phe Ser Glu Gln Tyr Ala Arg Arg Ser Asp Thr Phe Phe Cys Val Asp
    50                  55                  60

Lys Ser Val Thr Ser Val Val Ile Lys Gly Leu Ala Asp His Lys Asp
65                  70                  75                  80

Ser Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Glu Asn Asp
        115                 120                 125

Phe Ala Gly Gln Asp Gln Ser Ile Ser Leu Asp Glu Ile Lys Glu Ser
    130                 135                 140

Thr Ala Asn Met
145

<210> SEQ ID NO 60
<211> LENGTH: 144
<212> TYPE: PRT
<213> ORGANISM: Medicago truncatula
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 60

Met Thr Ser Gln Ala Ser Thr Phe Ala Val Ser Val Ser Ser Ala Pro
1               5                   10                  15

Ser Pro Leu Arg Arg Arg Arg Thr Phe Pro Val Val Arg Ala Gln Leu
            20                  25                  30

Glu Pro Ser Asp Lys Ser Val Glu Ile Met Arg Lys Phe Ser Glu Gln
        35                  40                  45

Tyr Ala Arg Lys Ser Gly Thr Phe Phe Cys Ser Asp Lys Gly Val Thr
    50                  55                  60

Ala Val Val Ile Lys Gly Leu Ala Asp His Lys Asp Ser Leu Gly Ala
65                  70                  75                  80

Pro Leu Cys Pro Cys Arg His Tyr Asp Asp Lys Ala Ala Glu Ala Ala
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asp
        115                 120                 125

Glu Gln Thr Ile Thr Leu Asp Glu Ile Lys Glu Ser Thr Ala Asn Met
    130                 135                 140

<210> SEQ ID NO 61
<211> LENGTH: 146
<212> TYPE: PRT
<213> ORGANISM: Capsella rubella
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 61

Met Asn Leu Gln Ala Val Ser Cys Ser Phe Gly Phe Val Ser Ser Pro
1               5                   10                  15

Leu Gly Val Thr Pro Arg Thr Ser Phe Arg Arg Phe Val Ile Arg Ala
            20                  25                  30

Lys Thr Glu Pro Ser Glu Lys Ser Ile Glu Ile Met Arg Lys Phe Ser
        35                  40                  45

Glu Gln Tyr Ala Arg Arg Ser Gly Thr Tyr Phe Cys Val Asp Lys Gly
    50                  55                  60

Val Thr Ser Val Val Ile Lys Gly Leu Ala Glu His Lys Asp Ser Tyr
65                  70                  75                  80

Gly Ala Pro Leu Cys Pro Cys Arg His Tyr Asp Asp Lys Ala Ala Glu
                85                  90                  95

Val Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Lys Asp Gln Thr Ile Thr Ser Asp Glu Ile Lys Glu Thr Thr Ala
    130                 135                 140

Asn Met
145

<210> SEQ ID NO 62
<211> LENGTH: 151
<212> TYPE: PRT
<213> ORGANISM: Daucus carota
<220> FEATURE:
<221> NAME/KEY: MISC_FEATURE
<222> LOCATION: (1)..(151)
<223> OTHER INFORMATION: ferredoxin-thioredoxin reductase

<400> SEQUENCE: 62

Met Arg Ser Leu Gln Ala Ser Thr Ser Tyr Thr Thr Ser Leu Ser Ser
1               5                   10                  15

Ala Val Pro Ser Val Ala Asn Tyr Ser Pro Arg Thr Leu His His Arg
            20                  25                  30

His Val Ile Ser Ala Lys Gly Glu Pro Thr Glu Lys Ser Val Glu Ile
        35                  40                  45

Met Arg Lys Phe Ser Glu Gln Tyr Ala Arg Arg Ser Gly Thr Tyr Phe
    50                  55                  60

Cys Val Asp Lys Ser Val Thr Ser Val Val Ile Lys Gly Leu Ala Asp
65                  70                  75                  80

His Lys Asp Thr Leu Gly Ala Pro Leu Cys Pro Cys Arg His Tyr Asp
                85                  90                  95

```
Asp Lys Ala Ala Glu Ala Val Gln Gly Phe Trp Asn Cys Pro Cys Val
                100                 105                 110

Pro Met Arg Glu Arg Lys Glu Cys His Cys Met Leu Phe Leu Thr Thr
            115                 120                 125

Asp Asn Asp Phe Ala Gly Gln Asp Gln Ala Ile Ser Leu Glu Glu Ile
130                 135                 140

Lys Glu Thr Thr Ala Gly Met
145                 150

<210> SEQ ID NO 63
<211> LENGTH: 144
<212> TYPE: PRT
<213> ORGANISM: Glycine max
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 63

Met Thr Thr Gln Ala Ser Thr Phe Ala Val Ala Val Pro Ser Val Thr
1               5                   10                  15

Thr Pro Phe Arg Ser His Arg Asn Pro Phe Val Val Arg Ala Gln Ala
            20                  25                  30

Glu Pro Ser Asp Lys Ser Val Glu Ile Met Arg Lys Phe Ser Glu Gln
        35                  40                  45

Tyr Ala Arg Lys Ser Gly Thr Tyr Phe Cys Val Asp Lys Gly Val Thr
    50                  55                  60

Ser Val Val Ile Lys Gly Leu Ala Asp His Lys Asp Thr Leu Gly Ala
65                  70                  75                  80

Pro Leu Cys Pro Cys Arg His Tyr Asp Asp Lys Ala Ala Glu Val Ala
                85                  90                  95

Gln Gly Phe Arg Asn Cys Pro Cys Val Pro Met Arg Glu Arg Lys Glu
            100                 105                 110

Cys His Cys Met Leu Phe Leu Thr Pro Asp Asn Asp Phe Ala Gly Asn
        115                 120                 125

Glu Gln Thr Ile Thr Leu Asp Glu Ile Lys Glu Ser Thr Ala Asn Met
    130                 135                 140

<210> SEQ ID NO 64
<211> LENGTH: 148
<212> TYPE: PRT
<213> ORGANISM: Solanum tuberosum
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 64

Met Arg Thr Leu Gln Ala Ser Thr Ser Tyr Ser Val Gly Phe Gly Ile
1               5                   10                  15

Ser Ser Phe Ala Thr Arg Pro Lys Pro Ser Thr His Arg Cys Leu Thr
            20                  25                  30

Val Ala Lys Met Glu Pro Ser Glu Lys Ser Val Glu Ile Met Arg Lys
        35                  40                  45

Phe Ser Glu Gln Tyr Ala Arg Arg Ser Glu Thr Tyr Phe Cys Met Asp
    50                  55                  60

Lys Gly Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Ala
```

```
                    85                  90                  95

Ala Glu Ala Gln Gln Gly Phe Trp Asn Cys Pro Cys Val Pro Met Arg
                100                 105                 110

Glu Arg Lys Glu Cys His Cys Met Leu Phe Leu Thr Pro Asp Asn Asp
            115                 120                 125

Phe Ala Gly Glu Glu Gln Thr Ile Ser Met Glu Glu Ile Lys Glu Thr
        130                 135                 140

Thr Ala Asn Met
145

<210> SEQ ID NO 65
<211> LENGTH: 150
<212> TYPE: PRT
<213> ORGANISM: Sesamum indicum
<220> FEATURE:
<221> NAME/KEY: MISC_FEATURE
<222> LOCATION: (1)..(150)
<223> OTHER INFORMATION: ferredoxin-thioredoxin reductase

<400> SEQUENCE: 65

Met Arg Ala Leu Gln Ala Ser Thr Ser Tyr Ser Val Ala Phe Ala Ile
1               5                   10                  15

Ser Ser Val Ala Pro Leu Pro Ser Leu Pro Arg Pro Arg Gln Arg His
                20                  25                  30

Val Ile Ser Ala Asn His Glu Pro Thr Glu Lys Ser Val Glu Ile Met
            35                  40                  45

Arg Lys Phe Ser Glu Gln Tyr Ala Arg Arg Ser Gly Thr Tyr Phe Cys
        50                  55                  60

Val Asp Lys Gly Val Thr Ser Val Val Ile Lys Gly Leu Ala Glu His
65                  70                  75                  80

Lys Asp Thr Leu Gly Ala Pro Leu Cys Pro Cys Arg His Tyr Asp Asp
                85                  90                  95

Lys Ala Ala Glu Ala Gln Gln Gly Phe Trp Asn Cys Pro Cys Val Pro
                100                 105                 110

Met Arg Glu Arg Lys Glu Cys His Cys Met Leu Phe Leu Thr Pro Asp
            115                 120                 125

Asn Asp Phe Ala Gly Gln Glu Gln Asn Ile Ser Leu Glu Glu Ile Lys
        130                 135                 140

Glu Thr Thr Ala Asn Leu
145                 150

<210> SEQ ID NO 66
<211> LENGTH: 144
<212> TYPE: PRT
<213> ORGANISM: Cajanus cajan
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 66

Met Thr Ala Gln Ala Ser Ser Phe Ser Val Ala Val Ser Ser Val Ala
1               5                   10                  15

Thr Pro Phe Arg Arg His Arg Asn Pro Phe Val Val Arg Ala Gln Ala
                20                  25                  30

Glu Pro Ser Asp Lys Ser Val Glu Ile Met Arg Lys Phe Ser Glu Gln
            35                  40                  45

Tyr Ala Arg Lys Ser Gly Thr Tyr Phe Cys Val Asp Lys Gly Val Thr
        50                  55                  60
```

```
Ser Val Val Ile Lys Gly Leu Ala Asp His Lys Asp Ser Leu Gly Ala
 65                  70                  75                  80

Pro Leu Cys Pro Cys Arg His Tyr Asp Asp Lys Ala Ala Glu Val Ala
                 85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Asp
        115                 120                 125

Glu Gln Thr Ile Thr Leu Asp Glu Ile Lys Glu Ser Thr Ala Asn Met
130                 135                 140

<210> SEQ ID NO 67
<211> LENGTH: 148
<212> TYPE: PRT
<213> ORGANISM: Juglans regia
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 67

Met Thr Leu Gln Ala Gln Ala Ser Ser Ser Phe Ala Val Gly Ile
1               5                   10                  15

Pro Ser Phe Thr Ser Pro Leu Gly Gly Ser Arg His Arg Leu Val Val
                20                  25                  30

Arg Ala Lys Val Glu Pro Ser Asp Lys Ser Val Glu Ile Met Arg Lys
            35                  40                  45

Phe Ser Glu Gln Tyr Ala Arg Lys Ser Gly Thr Tyr Phe Cys Val Asp
 50                  55                  60

Lys Gly Val Thr Ser Val Val Ile Lys Gly Leu Ala Asp His Lys Asp
 65                  70                  75                  80

Ser Leu Gly Ala Pro Leu Cys Pro Cys Arg His Tyr Asp Asp Lys Pro
                85                  90                  95

Ala Glu Ala Gly Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
        115                 120                 125

Phe Ala Gly Lys Glu Gln Thr Ile Ser Leu Glu Glu Ile Arg Glu Ser
130                 135                 140

Thr Ala Asn Met
145

<210> SEQ ID NO 68
<211> LENGTH: 146
<212> TYPE: PRT
<213> ORGANISM: Pyrus x bretschneideri
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 68

Met Thr Leu Gln Leu Gln Ala Pro Ser Phe Ala Ala Ser Ile Ser Ser
1               5                   10                  15

Phe Val Ser Pro Leu Asn Arg Pro Thr Arg Arg Pro Val Ile Arg Ala
                20                  25                  30

Lys Ala Glu Pro Ser Asp Lys Ser Val Glu Ile Met Arg Lys Phe Ser
            35                  40                  45
```

Glu Gln Tyr Ala Arg Lys Ser Gly Thr Tyr Phe Cys Val Asp Lys Gly
        50              55                  60

Val Thr Ser Val Val Ile Lys Gly Leu Ala Asp His Lys Asp Ser Leu
65                  70                  75                  80

Gly Ala Pro Leu Cys Pro Cys Arg His Tyr Asp Asp Lys Pro Ala Glu
                85                  90                  95

Ala Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
            115                 120                 125

Gly Pro Glu Gln Ala Ile Ser Leu Glu Glu Ile Arg Glu Ser Thr Ala
    130                 135                 140

Asn Met
145

<210> SEQ ID NO 69
<211> LENGTH: 148
<212> TYPE: PRT
<213> ORGANISM: Elaeis guineensis
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 69

Met Ala Ala Met Ser Thr Arg Thr Ala Phe His Gly Val Pro Leu Pro
1               5                   10                  15

Ile Phe Gln Pro Ala Ser Pro Pro Ser Arg Pro Tyr Arg Leu Leu Val
                20                  25                  30

Arg Ser Lys Val Glu Pro Ser Glu Lys Ser Val Asp Ile Met Arg Arg
            35                  40                  45

Phe Ser Glu Lys Tyr Ala Gln Gln Ser Gly Thr Tyr Phe Cys Ala Asp
    50                  55                  60

Lys Gly Val Thr Ser Val Val Ile Lys Gly Leu Ala Asp His Lys Asp
65                  70                  75                  80

Ser Leu Gly Ala Pro Leu Cys Pro Cys Arg His Tyr Asp Asp Lys Ala
                85                  90                  95

Ala Glu Val Gly Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
        115                 120                 125

Phe Ala Gly Thr Glu Gln Thr Ile Thr Leu Asp Glu Ile Lys Glu Ala
    130                 135                 140

Thr Ser Lys Val
145

<210> SEQ ID NO 70
<211> LENGTH: 149
<212> TYPE: PRT
<213> ORGANISM: Erythranthe guttata
<220> FEATURE:
<221> NAME/KEY: MISC_FEATURE
<222> LOCATION: (1)..(149)
<223> OTHER INFORMATION: ferredoxin-thioredoxin reductase

<400> SEQUENCE: 70

Met Thr Ala Leu Gln Ala Ser Thr Ser Tyr Ser Val Gly Phe Ala Ile
1               5                   10                  15

Ser Ser Ala Ala Pro Pro Pro Leu Pro Ser Arg His Leu Arg His Gly

```
                   20                  25                  30
Val Val Ala Lys Val Glu Pro Thr Glu Lys Ser Val Glu Val Met Arg
                35                  40                  45

Lys Phe Ser Glu Gln Tyr Ala Arg Arg Ser Gly Thr Tyr Phe Cys Val
             50                  55                  60

Asp Lys Gly Val Thr Ser Val Val Ile Lys Gly Leu Ala Asp His Lys
 65                  70                  75                  80

Asp Ser Leu Gly Ala Pro Leu Cys Pro Cys Arg His Tyr Asp Asp Lys
                 85                  90                  95

Ala Ala Glu Ala Gln Gln Gly Phe Trp Asn Cys Pro Cys Val Pro Met
                100                 105                 110

Arg Glu Arg Lys Glu Cys His Cys Met Leu Phe Leu Thr Pro Asp Asn
            115                 120                 125

Asp Phe Ala Gly Gln Glu Gln Val Ile Ser Met Glu Glu Ile Arg Glu
        130                 135                 140

Thr Thr Ala Asn Met
145

<210> SEQ ID NO 71
<211> LENGTH: 150
<212> TYPE: PRT
<213> ORGANISM: Populus trichocarpa x Populus deltoides
<220> FEATURE:
<221> NAME/KEY: MISC_FEATURE
<222> LOCATION: (1)..(150)
<223> OTHER INFORMATION: ferredoxin-thioredoxin reductase

<400> SEQUENCE: 71

Met Asn Trp Ser Cys Ser Thr Ala Thr Cys Gly Ile Ser Ser Ser
 1               5                  10                  15

Ser Ser Cys Phe Ser Cys Pro Pro Lys Thr Pro Ser Phe Arg Ser Val
                 20                  25                  30

Ile Arg Ala Ser Lys Val Glu Pro Ser Asp Lys Ser Val Glu Ile Met
             35                  40                  45

Arg Lys Phe Ser Glu Gln Tyr Ala Arg Lys Ser Gly Thr Tyr Phe Cys
 50                  55                  60

Val Asp Lys Gly Val Thr Ser Val Val Ile Lys Gly Leu Ala Asp His
 65                  70                  75                  80

Lys Asp Ser Leu Gly Ala Pro Leu Cys Pro Cys Arg His Tyr Asp Asp
                 85                  90                  95

Lys Ala Ala Glu Ala Gly Gln Gly Phe Trp Asn Cys Pro Cys Val Pro
                100                 105                 110

Met Arg Glu Arg Lys Glu Cys His Cys Met Leu Phe Leu Thr Pro Asp
            115                 120                 125

Asn Asp Phe Ala Gly Lys Asp Gln Thr Ile Ser Leu Glu Glu Ile Arg
        130                 135                 140

Glu Thr Thr Ala Asn Met
145                 150

<210> SEQ ID NO 72
<211> LENGTH: 145
<212> TYPE: PRT
<213> ORGANISM: Vigna angularis
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 72
```

```
Met Thr Thr Gln Ala Ser Ala Phe Ser Leu Ala Ala Pro Ser Val Ala
1               5                   10                  15

Thr Pro Phe Arg Arg His Arg Asn Pro Leu Leu Val Arg Ala Ala
            20                  25                  30

Val Glu Pro Ser Asp Lys Ser Val Glu Ile Met Arg Lys Phe Ser Glu
            35                  40                  45

Gln Tyr Ala Arg Lys Ser Gly Thr Tyr Phe Cys Val Asp Lys Gly Val
    50                  55                  60

Thr Ser Val Val Ile Lys Gly Leu Ala Asp His Lys Asp Ser Leu Gly
65                  70                  75                  80

Ala Pro Leu Cys Pro Cys Arg His Tyr Asp Asp Lys Ala Ala Glu Ala
                85                  90                  95

Ala Gln Gly Phe Trp Asn Cys Pro Cys Val Pro Met Arg Glu Arg Lys
                100                 105                 110

Glu Cys His Cys Met Leu Phe Leu Thr Pro Asp Asn Asp Phe Ala Gly
            115                 120                 125

Asp Glu Gln Ala Ile Thr Leu Glu Glu Ile Lys Glu Ser Thr Ala Asn
    130                 135                 140

Met
145

<210> SEQ ID NO 73
<211> LENGTH: 144
<212> TYPE: PRT
<213> ORGANISM: Cucumis sativus
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 73

Met Ile Leu Gln Ala Ser Ser Phe Asn Ile Ala Val Pro Leu Tyr Gly
1               5                   10                  15

Ser Ser Leu Gly Cys Ser Arg His Arg His Val Val Arg Ala Gln Ala
            20                  25                  30

Glu Pro Ser Glu Lys Ser Val Glu Ile Met Arg Lys Phe Ser Glu Gln
            35                  40                  45

Tyr Ala Arg Lys Ser Gly Thr Tyr Phe Cys Val Asp Lys Gly Val Thr
    50                  55                  60

Ala Val Val Ile Lys Gly Leu Ala Asp His Lys Asp Thr Leu Gly Ala
65                  70                  75                  80

Pro Leu Cys Pro Cys Arg His Tyr Asp Asp Lys Pro Ala Glu Val Ala
                85                  90                  95

Gln Gly Phe Trp Asn Cys Pro Cys Val Pro Met Arg Glu Arg Lys Glu
                100                 105                 110

Cys His Cys Met Leu Phe Leu Thr Pro Glu Asn Asp Phe Ala Gly Asn
            115                 120                 125

Asp Gln Ala Ile Ser Leu Glu Asp Ile Arg Ala Thr Thr Ala Asn Met
    130                 135                 140

<210> SEQ ID NO 74
<211> LENGTH: 145
<212> TYPE: PRT
<213> ORGANISM: Gossypium raimondii
<220> FEATURE:
<221> NAME/KEY: MISC_FEATURE
<222> LOCATION: (1)..(145)
<223> OTHER INFORMATION: ferredoxin-thioredoxin reductase
```

<400> SEQUENCE: 74

Met Thr Leu Gln Ala Thr Ser Cys Asn Phe Gly Ala Ile Ser Ser Leu
1               5                   10                  15

Leu Arg Pro Pro Lys Ile Ser Arg His Arg Phe Val Ile Arg Ala Glu
            20                  25                  30

Val Glu Pro Ser Glu Lys Ser Val Glu Ile Met Arg Lys Phe Ser Glu
        35                  40                  45

Gln Tyr Ala Arg Arg Ser Gly Thr Tyr Phe Cys Met Asp Lys Gly Val
    50                  55                  60

Thr Ser Val Val Ile Lys Gly Leu Ala Glu His Lys Asp Ser Leu Gly
65                  70                  75                  80

Ala Pro Leu Cys Pro Cys Arg His Tyr Asp Asp Lys Ala Ala Glu Val
                85                  90                  95

Ser Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Thr Ile Thr Leu Glu Glu Ile Lys Glu Thr Thr Ala Asn
    130                 135                 140

Met
145

<210> SEQ ID NO 75
<211> LENGTH: 145
<212> TYPE: PRT
<213> ORGANISM: Nelumbo nucifera
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 75

Met Thr Val Gln Ala Ser Phe Tyr Ser Val Gly Val Pro Ser Phe Ala
1               5                   10                  15

Ala Pro Pro Pro Asn Arg Ser Arg His Val Ile Arg Ala Lys Ala Lys
            20                  25                  30

Val Glu Pro Ser Glu Lys Ser Val Glu Ile Met Arg Lys Phe Ser Glu
        35                  40                  45

Gln Tyr Ala Arg Lys Ser Gly Thr Tyr Phe Cys Val Asp Lys Gly Val
    50                  55                  60

Thr Ser Val Val Ile Lys Gly Leu Ala Asp His Lys Asp Ser Leu Gly
65                  70                  75                  80

Ala Pro Leu Cys Pro Cys Arg His Tyr Asp Asp Lys Ala Ala Glu Ala
                85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Lys Glu Gln Ala Ile Ser Leu Glu Glu Ile Arg Glu Ala Thr Ala Asn
    130                 135                 140

Met
145

<210> SEQ ID NO 76
<211> LENGTH: 144
<212> TYPE: PRT

```
<213> ORGANISM: Spinacia oleracea
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 76

Met Lys Ala Leu Gln Ala Ser Ile Ala Tyr Ser Phe Pro Ile Ser Ser
1               5                   10                  15

Pro Ala Ala Ser Pro Arg Arg Phe Ser Arg Val Ile Arg Ala Gln Ala
            20                  25                  30

Asp Pro Ser Asp Lys Ser Met Glu Val Met Arg Lys Phe Ser Glu Gln
        35                  40                  45

Phe Cys Arg Lys Ser Asp Thr Tyr Phe Cys Val Asp Lys Ser Val Thr
    50                  55                  60

Ala Val Val Ile Lys Gly Leu Ala Asp His Arg Asp Thr Leu Gly Ala
65                  70                  75                  80

Pro Leu Cys Pro Cys Arg His Tyr Asp Asp Lys Glu Ala Glu Ala Lys
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Lys
        115                 120                 125

Glu Gln Thr Ile Thr Leu Asp Glu Ile Arg Glu Val Thr Ser Asn Met
    130                 135                 140

<210> SEQ ID NO 77
<211> LENGTH: 146
<212> TYPE: PRT
<213> ORGANISM: Malus domestica
<220> FEATURE:
<221> NAME/KEY: MISC_FEATURE
<222> LOCATION: (1)..(146)
<223> OTHER INFORMATION: ferredoxin-thioredoxin reductase
<220> FEATURE:
<221> NAME/KEY: MISC_FEATURE
<222> LOCATION: (8)..(8)
<223> OTHER INFORMATION: Xaa refers to any amino acid

<400> SEQUENCE: 77

Met Thr Leu Gln Leu Gln Ala Xaa Ser Phe Gly Ala Ser Ile Ala Ser
1               5                   10                  15

Phe Val Ser Pro Leu Asn Arg Ser Thr Arg Arg Pro Val Ile Ile Ala
            20                  25                  30

Asn Ala Glu Pro Ser Asp Lys Ser Val Glu Ile Met Arg Lys Phe Ser
        35                  40                  45

Glu Gln Tyr Ala Arg Lys Ser Gly Thr Tyr Phe Cys Val Asp Lys Gly
    50                  55                  60

Val Thr Ser Val Val Ile Lys Gly Leu Ala Asp His Lys Asp Ser Leu
65                  70                  75                  80

Gly Ala Pro Leu Cys Pro Cys Arg His Tyr Asp Asp Lys Pro Ala Glu
                85                  90                  95

Ala Gly Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Pro Glu Gln Ala Ile Ser Leu Glu Glu Ile Lys Glu Ser Thr Ala
    130                 135                 140

Asn Met
```

```
145

<210> SEQ ID NO 78
<211> LENGTH: 145
<212> TYPE: PRT
<213> ORGANISM: Gossypium arboreum
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 78

Met Thr Leu Gln Ala Ser Phe Phe Asn Phe Gly Ser Ile Phe Ser Leu
1               5                   10                  15

Pro Cys Pro Pro Arg Thr Ser Arg Gln Arg Phe Val Ile Arg Ala Lys
            20                  25                  30

Val Glu Pro Ser Glu Lys Ser Val Glu Ile Met Arg Lys Phe Ser Glu
        35                  40                  45

Gln Tyr Ala Arg Arg Ser Gly Thr Tyr Phe Cys Met Asp Lys Gly Val
    50                  55                  60

Thr Ser Val Val Ile Lys Gly Leu Ala Glu His Lys Asp Thr Leu Gly
65                  70                  75                  80

Ala Pro Leu Cys Pro Cys Arg His Tyr Asp Asp Lys Ala Ala Glu Val
                85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Ser Ile Thr Leu Glu Glu Ile Lys Glu Thr Thr Thr Asn
    130                 135                 140

Met
145

<210> SEQ ID NO 79
<211> LENGTH: 149
<212> TYPE: PRT
<213> ORGANISM: Solanum lycopersicum
<220> FEATURE:
<221> NAME/KEY: MISC_FEATURE
<222> LOCATION: (1)..(149)
<223> OTHER INFORMATION: ferredoxin-thioredoxin reductase

<400> SEQUENCE: 79

Met Arg Thr Leu Gln Ala Ser Thr Ser Tyr Ser Val Gly Phe Gly Ile
1               5                   10                  15

Ser Ser Phe Ala Thr Arg Pro Lys Pro Ser Ser Thr His Arg Cys Leu
            20                  25                  30

Thr Val Ala Lys Met Glu Pro Ser Glu Lys Ser Val Glu Ile Met Arg
        35                  40                  45

Lys Phe Ser Glu Gln Tyr Ala Arg Arg Ser Gly Thr Tyr Phe Cys Met
    50                  55                  60

Asp Lys Gly Val Thr Ser Val Val Ile Lys Gly Leu Ala Glu His Lys
65                  70                  75                  80

Asp Thr Leu Gly Ala Pro Leu Cys Pro Cys Arg His Tyr Asp Asp Lys
                85                  90                  95

Ala Ala Glu Ala Gln Gln Gly Phe Trp Asn Cys Pro Cys Val Pro Met
            100                 105                 110

Arg Glu Arg Lys Glu Cys His Cys Met Leu Phe Leu Thr Pro Asp Asn
        115                 120                 125
```

Asp Phe Ala Gly Glu Glu Gln Thr Ile Thr Met Glu Glu Ile Lys Glu
            130                 135                 140

Thr Thr Ala Asn Met
145

<210> SEQ ID NO 80
<211> LENGTH: 145
<212> TYPE: PRT
<213> ORGANISM: Morus notabilis
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 80

Met Thr Val Gln Ala Ser Thr Ser Phe Ser Phe Gly Ile Ser Ser Phe
1               5                   10                  15

Val Ile Pro Pro Ala Arg Ser Arg His Arg Ser Val Ile Arg Ala Gln
            20                  25                  30

Val Glu Pro Ser Glu Lys Ser Val Glu Ile Met Arg Lys Phe Ser Glu
        35                  40                  45

Gln Tyr Ala Arg Arg Ser Gly Thr Tyr Phe Cys Val Asp Lys Gly Val
    50                  55                  60

Thr Ser Val Val Ile Lys Gly Leu Ala Asp His Lys Asp Gln Leu Gly
65                  70                  75                  80

Ala Pro Leu Cys Pro Cys Arg His Tyr Asp Asp Lys Ala Ala Glu Ala
                85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Glu Gln Thr Val Thr Leu Glu Glu Ile Lys Glu Ser Thr Ala Asn
    130                 135                 140

Met
145

<210> SEQ ID NO 81
<211> LENGTH: 175
<212> TYPE: PRT
<213> ORGANISM: Triticum urartu
<220> FEATURE:
<221> NAME/KEY: MISC_FEATURE
<222> LOCATION: (1)..(175)
<223> OTHER INFORMATION: ferredoxin-thioredoxin reductase

<400> SEQUENCE: 81

Met Ser Ile Thr Ser Thr Ala Ala Ala Ala Gly Ser Pro Val Tyr
1               5                   10                  15

Thr Pro Leu Val Pro Arg Gly Gly Arg Arg Ser Arg Cys Ala Val Arg
            20                  25                  30

Ala Gln Ala Ala Gly Glu Gly Ala Ala Ala Asp Gly Ala Ala Ser
        35                  40                  45

Glu His Lys Ser Leu Glu Ile Met Arg Lys Phe Ser Glu Gln Tyr Ala
    50                  55                  60

Arg Arg Ser Ser Thr Phe Phe Cys Ser Asp Lys Ser Val Thr Ala Val
65                  70                  75                  80

Val Ile Lys Gly Leu Ala Asp His Lys Glu Gln Leu Gly Ala Pro Leu
                85                  90                  95

```
Cys Pro Cys Arg Gln Val Gly Gln Ser Tyr Arg His Tyr Asp Asp Lys
                100                 105                 110

Ala Ala Glu Ala Ala Gln Gly Phe Trp Asn Cys Pro Cys Val Pro Met
            115                 120                 125

Arg Glu Arg Lys Glu Cys His Cys Met Leu Phe Leu Thr Pro Asp Asn
        130                 135                 140

Asp Phe Ala Gly Glu Asp Gln Ala Arg Leu Arg Phe Leu Ser Val Leu
145                 150                 155                 160

Ser Ala Ile Ser Leu Glu Glu Ile Lys Glu Ala Thr Ser Lys Tyr
                165                 170                 175

<210> SEQ ID NO 82
<211> LENGTH: 148
<212> TYPE: PRT
<213> ORGANISM: Nicotiana tomentosiformis
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 82

Met Arg Thr Leu Gln Ala Ser Thr Ser Tyr Ser Val Gly Phe Gly Ile
1               5                   10                  15

Ser Ser Phe Ala Thr Leu Pro Lys Pro Ser Thr Arg Arg Asp Val Ala
                20                  25                  30

Val Ala Lys Met Glu Pro Ser Glu Lys Ser Val Glu Ile Met Arg Lys
            35                  40                  45

Phe Ser Glu Gln Tyr Ala Arg Arg Ser Gly Thr Tyr Phe Cys Met Asp
    50                  55                  60

Lys Gly Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
        115                 120                 125

Phe Ala Gly Glu Glu Gln Ala Ile Ser Met Glu Glu Ile Lys Glu Thr
    130                 135                 140

Thr Ala Asn Met
145

<210> SEQ ID NO 83
<211> LENGTH: 210
<212> TYPE: PRT
<213> ORGANISM: Zostera marina
<220> FEATURE:
<221> NAME/KEY: MISC_FEATURE
<222> LOCATION: (1)..(210)
<223> OTHER INFORMATION: ferredoxin-thioredoxin reductase

<400> SEQUENCE: 83

Met Asp Gly Pro Arg Leu Leu Leu Pro Asn Ala Val Pro Ile Phe Leu
1               5                   10                  15

Ala Lys Leu Arg Pro His Arg Leu Ile Glu Pro Gln Asn Gln Lys Arg
                20                  25                  30

Glu Arg Arg Thr Lys Arg Ile Leu Glu Gln Gly Cys Leu Ser Val Ala
            35                  40                  45

Met Ser Ile Val Asn Arg Thr Ser Phe Tyr Gly Val Ala Ile Pro Ser
```

```
            50                  55                  60
Ser Thr Leu Thr Ser Thr Val Arg Ala Arg Pro Phe Ser Thr Ile His
 65                  70                  75                  80

Tyr Pro Pro Arg His Gly Leu Pro Thr Gly Ile Arg Ala Glu Gln Ser
                 85                  90                  95

Ala Val Asp Pro Ala Asp Lys Ser Val Glu Thr Met Arg Lys Phe Ser
                100                 105                 110

Glu Gln Tyr Ala Arg Arg Ser Asp Thr Phe Phe Cys Val Asp Lys Ser
            115                 120                 125

Val Thr Ser Val Val Ile Lys Gly Leu Ala Asp His Lys Thr Ser Leu
130                 135                 140

Gly Ala Pro Leu Cys Pro Cys Arg His Tyr Asp Asp Lys Ala Ala Glu
145                 150                 155                 160

Ala Lys Gln Gly Phe Trp Asn Cys Pro Cys Val Pro Met Arg Glu Arg
                165                 170                 175

Lys Glu Cys His Cys Met Leu Phe Leu Thr Pro Asp Asn Asp Phe Ala
                180                 185                 190

Gly Thr Asp Gln Thr Ile Thr Met Glu Glu Ile Ser Glu Thr Val Asn
            195                 200                 205

Gly Ala
210

<210> SEQ ID NO 84
<211> LENGTH: 144
<212> TYPE: PRT
<213> ORGANISM: Suaeda glauca
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 84

Met Lys Ser Leu Gln Ala Ser Thr Ala Tyr Ser Phe Pro Ile Ser Ser
  1               5                  10                  15

Pro Ser Ile Pro Pro Lys Arg Phe Ser Arg Val Ile Arg Ala Gln Val
                 20                  25                  30

Glu Pro Ser Asp Lys Ser Met Glu Val Met Arg Lys Phe Ser Glu Gln
             35                  40                  45

Phe Cys Arg Lys Ser Gly Thr Tyr Phe Cys Val Asp Lys Ser Val Thr
 50                  55                  60

Ala Val Val Ile Lys Gly Leu Ala Asp His Arg Asp Thr Leu Gly Ala
 65                  70                  75                  80

Pro Leu Cys Pro Cys Arg His Tyr Asp Asp Lys Ala Ala Glu Ala Ser
                 85                  90                  95

Gln Gly Phe Trp Asn Cys Pro Cys Val Pro Met Arg Glu Arg Lys Glu
                100                 105                 110

Cys His Cys Met Leu Phe Leu Thr Pro Asp Asn Asp Phe Ala Gly Lys
            115                 120                 125

Asp Gln Thr Ile Thr Leu Asp Glu Ile Arg Glu Val Thr Ala Asn Met
130                 135                 140

<210> SEQ ID NO 85
<211> LENGTH: 145
<212> TYPE: PRT
<213> ORGANISM: Gossypium hirsutum
<220> FEATURE:
<221> NAME/KEY: MISC_FEATURE
<222> LOCATION: (1)..(145)
```

<223> OTHER INFORMATION: ferredoxin-thioredoxin reductase

<400> SEQUENCE: 85

```
Met Thr Leu Gln Ala Thr Ser Cys Asn Phe Gly Ala Ile Ser Ser Leu
1               5                   10                  15

Leu Arg Pro Pro Lys Ile Ser Arg His Arg Phe Val Ile Arg Ala Glu
            20                  25                  30

Val Glu Pro Ser Glu Lys Ser Val Glu Ile Met Arg Lys Phe Ser Glu
        35                  40                  45

Gln Tyr Ala Arg Arg Ser Gly Thr Tyr Phe Cys Met Asp Lys Gly Val
    50                  55                  60

Thr Ser Val Val Ile Lys Gly Leu Ala Glu His Lys Asp Ser Leu Gly
65                  70                  75                  80

Ala Pro Leu Cys Pro Cys Arg His Tyr Asp Asp Lys Ala Ala Glu Val
                85                  90                  95

Asn Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Thr Ile Thr Leu Glu Glu Ile Lys Glu Thr Thr Ala Asn
    130                 135                 140

Met
145
```

<210> SEQ ID NO 86
<211> LENGTH: 148
<212> TYPE: PRT
<213> ORGANISM: Nicotiana attenuata
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 86

```
Met Arg Thr Leu Gln Ala Ser Thr Ser Tyr Ser Val Gly Phe Gly Ile
1               5                   10                  15

Ser Ser Phe Ala Thr Leu Pro Lys Pro Ser Thr Arg Arg Asp Val Thr
            20                  25                  30

Val Ala Lys Met Glu Pro Ser Glu Lys Ser Val Glu Ile Met Arg Lys
        35                  40                  45

Phe Ser Glu Gln Tyr Ala Arg Arg Ser Gly Thr Tyr Phe Cys Met Asp
    50                  55                  60

Lys Gly Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Asp Asn Asp
        115                 120                 125

Phe Ala Gly Glu Glu Gln Ala Ile Ser Met Glu Glu Ile Lys Glu Thr
    130                 135                 140

Thr Ala Asn Met
145
```

<210> SEQ ID NO 87
<211> LENGTH: 146

```
<212> TYPE: PRT
<213> ORGANISM: Fragaria vesca
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 87

Met Thr Leu Gln Leu Gln Ala Pro Ser Phe Ala Ala Thr Ile Ser Ser
1               5                   10                  15

Leu Ala Ser Pro Leu Asn Arg Ser Thr Arg Arg Phe Val Ile Arg Ala
            20                  25                  30

Gln Val Glu Pro Thr Glu Lys Ser Val Glu Ile Met Arg Lys Phe Ser
        35                  40                  45

Glu Gln Tyr Ala Arg Lys Ser Gly Thr Tyr Phe Cys Val Asp Lys Gly
    50                  55                  60

Val Thr Ser Val Val Ile Lys Gly Leu Ala Asp His Lys Asp Ser Leu
65                  70                  75                  80

Gly Ala Pro Leu Cys Pro Cys Arg His Tyr Asp Asp Lys Pro Ala Glu
                85                  90                  95

Ala Gly Gln Gly Phe Trp Asn Cys Pro Cys Val Pro Met Arg Glu Arg
            100                 105                 110

Lys Glu Cys His Cys Met Leu Phe Leu Thr Pro Glu Asn Asp Phe Ala
        115                 120                 125

Gly Lys Glu Gln Thr Ile Thr Leu Glu Glu Ile Arg Glu Ser Thr Ala
    130                 135                 140

Asn Met
145

<210> SEQ ID NO 88
<211> LENGTH: 148
<212> TYPE: PRT
<213> ORGANISM: Erythranthe guttata
<220> FEATURE:
<221> NAME/KEY: MISC_FEATURE
<222> LOCATION: (1)..(148)
<223> OTHER INFORMATION: ferredoxin-thioredoxin reductase

<400> SEQUENCE: 88

Met Arg Ala Leu Gln Ala Ser Thr Ser Tyr Ser Ile Ser Ser Phe Gly
1               5                   10                  15

Ile Ser Ser Ala Ala Pro Ser Pro Ser Arg Arg Arg His Val Val
            20                  25                  30

Phe Ser Lys Ala Glu Pro Thr Glu Lys Ser Val Glu Ile Met Arg Lys
        35                  40                  45

Phe Ser Glu Gln Tyr Ala Arg Arg Ser Asp Thr Tyr Phe Cys Val Asp
    50                  55                  60

Lys Gly Val Thr Ser Val Val Ile Lys Gly Leu Ala Glu His Lys Asp
65                  70                  75                  80

Thr Leu Gly Ala Pro Leu Cys Pro Cys Arg His Tyr Asp Asp Lys Ala
                85                  90                  95

Ala Glu Ala Gln Gln Gly Phe Trp Asn Cys Pro Cys Val Pro Met Arg
            100                 105                 110

Glu Arg Lys Glu Cys His Cys Met Leu Phe Leu Thr Pro Glu Asn Asp
        115                 120                 125

Phe Ala Gly Gln Asp Gln Thr Ile Thr Leu Glu Glu Ile Arg Glu Thr
    130                 135                 140

Thr Ser Asn Met
```

<210> SEQ ID NO 89
<211> LENGTH: 391
<212> TYPE: PRT
<213> ORGANISM: Punica granatum
<220> FEATURE:
<221> NAME/KEY: MISC_FEATURE
<222> LOCATION: (1)..(391)
<223> OTHER INFORMATION: ferredoxin-thioredoxin reductase

<400> SEQUENCE: 89

```
Met Lys Pro Val Ser Phe Leu Leu Cys Leu Ile Phe Leu Val Val Gly
1               5                   10                  15

Phe Arg Glu Ser Val Gln Gly Arg Pro Leu Ser Val Ser Lys Pro Asp
            20                  25                  30

Pro Arg Asn Ala Ala Thr Ala Arg Trp Leu Val Ala Gln Asn Ser
        35                  40                  45

Trp Gly Val Leu Asn Thr Ile Ser Ser Glu Leu Gly Gly Ala Pro Phe
    50                  55                  60

Gly Asn Val Val Ser Phe Ser Asp Gly Ser Pro Asn Glu Gly Arg Gly
65                  70                  75                  80

Ile Pro Tyr Phe Tyr Leu Thr Ala Leu Asp Pro Thr Ala Lys Asn Ala
                85                  90                  95

Leu Lys Asp Gly Arg Ala Ser Leu Thr Val Ser Glu Tyr Pro Leu Gly
            100                 105                 110

Thr Cys Gly Lys Ile Asp Pro Glu Asn Pro Thr Cys Ala Lys Leu Thr
        115                 120                 125

Leu Thr Gly Lys Leu Lys Ile Val Glu Glu Lys Ser Asp Glu Ala Gln
130                 135                 140

Tyr Ala Lys Ser Ala Leu Phe Thr Lys His Pro Glu Met Lys Thr Trp
145                 150                 155                 160

Pro Lys Ser His Lys Phe Gln Phe Phe Lys Leu Glu Ile Glu Asn Ile
                165                 170                 175

Phe Leu Ile Asp Trp Phe Gly Gly Pro Lys Pro Leu Thr Pro Glu Gln
            180                 185                 190

Tyr Leu His Pro Lys Thr Ile Glu Ser Gln Ser Ser Phe Leu Leu Leu
        195                 200                 205

Glu Ala Val Glu Ser Glu Val Ser Ser Lys Thr Leu Gln Val Trp Ser
210                 215                 220

Trp Lys Leu Ser Thr Ala Thr Leu Leu Ile Val Trp Lys Leu Arg Leu
225                 230                 235                 240

Gln Ser Ala Gln Glu Thr Met Thr Leu Gln Ala Ser Ser Phe Ala Val
                245                 250                 255

Gly Met Pro Ala Leu Ala Pro Pro Arg Leu Gly Arg Ser Arg His Ser
            260                 265                 270

Cys Val Val Arg Ala Lys Val Glu Pro Leu Asp Lys Ser Val Glu Ile
        275                 280                 285

Met Arg Lys Phe Ser Glu Gln Tyr Ala Arg Arg Ser Gly Thr Tyr Phe
290                 295                 300

Cys Val Asp Lys Gly Val Thr Ser Val Val Ile Lys Gly Leu Ala Asp
305                 310                 315                 320

His Lys Asp Ser Leu Gly Ala Pro Leu Cys Pro Cys Arg His Tyr Asp
                325                 330                 335

Asp Lys Ala Ala Glu Ala Ala Gln Gly Phe Trp Asn Cys Pro Cys Val
            340                 345                 350
```

-continued

```
Pro Met Arg Glu Arg Lys Glu Cys His Cys Met Leu Phe Leu Thr Pro
        355                 360                 365

Glu Asn Asp Phe Ala Gly Thr Asp Gln Ser Ile Ser Leu Glu Glu Ile
    370                 375                 380

Arg Glu Ser Thr Ala Asn Met
385                 390

<210> SEQ ID NO 90
<211> LENGTH: 146
<212> TYPE: PRT
<213> ORGANISM: Lupinus angustifolius
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 90

Met Met Thr Leu Gln Ala Ser Thr Phe Ala Val Ala Ile Pro Ser Ser
1               5                   10                  15

Ala Val Thr His Leu Arg Arg His Arg Asn Phe Ser Ala Ile Arg Ala
                20                  25                  30

Gln Val Glu Pro Ser Asp Lys Asn Val Glu Ile Met Arg Lys Phe Ser
            35                  40                  45

Glu Gln Tyr Ala Arg Lys Ser Gly Thr Tyr Phe Cys Val Asp Lys Gly
        50                  55                  60

Val Thr Ser Val Val Ile Lys Gly Leu Ala Asp His Lys Asp Ser Leu
65                  70                  75                  80

Gly Ala Pro Leu Cys Pro Cys Arg His Tyr Asp Asp Lys Ala Ala Glu
                85                  90                  95

Ala Ser Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Gln Glu Gln Thr Ile Thr Leu Asp Glu Ile Lys Glu Ser Ile Val
    130                 135                 140

Asn Met
145

<210> SEQ ID NO 91
<211> LENGTH: 145
<212> TYPE: PRT
<213> ORGANISM: Gossypium raimondii
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 91

Met Thr Leu Gln Ala Ser Phe Phe Asn Phe Gly Ser Ile Ser Ser Leu
1               5                   10                  15

Pro Cys Pro Pro Arg Thr Ser Arg Gln Arg Phe Val Ile Arg Ala Lys
                20                  25                  30

Val Glu Pro Ser Glu Lys Ser Val Glu Ile Met Arg Lys Phe Ser Glu
            35                  40                  45

Gln Tyr Ala Arg Arg Ser Gly Thr Tyr Phe Cys Val Asp Lys Gly Val
        50                  55                  60

Thr Ser Val Val Ile Lys Gly Leu Ala Glu His Lys Asp Thr Leu Gly
65                  70                  75                  80
```

Ala Pro Leu Cys Pro Cys Arg His Tyr Asp Asp Lys Ala Ala Glu Ala
                85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Ala Ile Thr Leu Glu Glu Ile Lys Glu Thr Thr Ala Asn
    130                 135                 140

Met
145

<210> SEQ ID NO 92
<211> LENGTH: 145
<212> TYPE: PRT
<213> ORGANISM: Theobroma cacao
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 92

Met Thr Leu Gln Ala Thr Ser Cys Asn Phe Gly Gly Ile Ser Ser Leu
1               5                   10                  15

Leu Cys Pro Pro Lys Thr Ser Leu His Arg Phe Val Ile Arg Ala Lys
            20                  25                  30

Val Glu Pro Ser Glu Lys Ser Val Glu Ile Met Arg Lys Phe Ser Glu
        35                  40                  45

Gln Tyr Ala Arg Arg Ser Gly Thr Tyr Phe Cys Met Asp Lys Gly Val
    50                  55                  60

Thr Ser Val Val Ile Lys Gly Leu Ala Glu His Lys Asp Thr Leu Gly
65                  70                  75                  80

Ala Pro Leu Cys Pro Cys Arg His Tyr Asp Asp Lys Ala Ala Glu Val
                85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Ser Ile Thr Ser Glu Glu Ile Lys Glu Thr Thr Ala Asn
    130                 135                 140

Met
145

<210> SEQ ID NO 93
<211> LENGTH: 145
<212> TYPE: PRT
<213> ORGANISM: Eutrema salsugineum
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 93

Met Asn Leu Gln Ala Val Ser Cys Ser Phe Gly Phe Val Ser Val Pro
1               5                   10                  15

Leu Val Ser Pro Arg Thr Ser Phe Arg Arg Phe Val Ile Arg Ala Lys
            20                  25                  30

Ser Glu Pro Ser Glu Lys Ser Val Glu Ile Met Arg Lys Phe Ser Glu
        35                  40                  45

Gln Tyr Ala Arg Arg Ser Gly Thr Tyr Phe Cys Val Asp Lys Gly Val

```
                50                  55                  60
Thr Ser Val Val Ile Lys Gly Leu Ala Glu His Lys Asp Ser His Gly
 65                  70                  75                  80

Ala Pro Leu Cys Pro Cys Arg His Tyr Asp Asp Lys Ala Ala Glu Val
                 85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Lys Asp Gln Thr Ile Thr Ser Glu Glu Ile Lys Glu Thr Thr Ala Asn
    130                 135                 140

Met
145

<210> SEQ ID NO 94
<211> LENGTH: 145
<212> TYPE: PRT
<213> ORGANISM: Herrania umbratica
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 94

Met Thr Leu Gln Ala Thr Ser Cys Asn Phe Gly Gly Ile Ser Ser Leu
 1               5                  10                  15

Leu Cys Pro Pro Lys Thr Ser Gln His Arg Phe Val Ile Arg Ala Lys
                 20                  25                  30

Val Glu Pro Ser Glu Lys Ser Val Glu Ile Met Arg Lys Phe Ser Glu
             35                  40                  45

Gln Tyr Ala Arg Arg Ser Gly Thr Tyr Phe Cys Met Asp Lys Gly Val
         50                  55                  60

Thr Ser Val Val Ile Lys Gly Leu Ala Glu His Lys Asp Thr Leu Gly
 65                  70                  75                  80

Ala Pro Leu Cys Pro Cys Arg His Tyr Asp Asp Lys Thr Ala Glu Val
                 85                  90                  95

Gly Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Ser Ile Thr Leu Glu Glu Ile Lys Glu Thr Thr Ala Asn
    130                 135                 140

Met
145

<210> SEQ ID NO 95
<211> LENGTH: 145
<212> TYPE: PRT
<213> ORGANISM: Gossypium hirsutum
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 95

Met Thr Leu Gln Ala Thr Ser Cys Asn Phe Gly Ala Ile Ser Ser Leu
 1               5                  10                  15

Leu Arg Pro Pro Lys Ile Ser Arg His Arg Phe Val Ile Arg Ala Glu
                 20                  25                  30
```

```
Val Glu Pro Ser Glu Lys Ser Val Glu Ile Met Arg Lys Phe Ser Glu
            35                  40                  45

Gln Tyr Ala Arg Arg Ser Gly Thr Tyr Phe Cys Met Asp Lys Gly Val
    50                  55                  60

Thr Ser Val Val Ile Lys Gly Leu Ala Glu His Lys Asp Ser Leu Gly
65                  70                  75                  80

Ala Pro Leu Cys Pro Cys Arg His Tyr Asp Asp Lys Ala Ala Glu Ala
                85                  90                  95

Ser Gln Gly Phe Trp Asn Cys Pro Cys Val Pro Met Arg Glu Arg Lys
                100                 105                 110

Glu Cys His Cys Met Leu Phe Leu Thr Pro Asp Asn Asp Phe Ala Gly
            115                 120                 125

Gln Asp Gln Thr Ile Thr Leu Glu Glu Ile Lys Glu Thr Thr Ala Asn
    130                 135                 140

Met
145

<210> SEQ ID NO 96
<211> LENGTH: 144
<212> TYPE: PRT
<213> ORGANISM: Raphanus sativus
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 96

Met Asn Pro Gln Ala Val Ser Cys Ser Phe Gly Phe Val Ser Ala Pro
1               5                   10                  15

Leu Val Ser Pro Arg Arg Thr Ser Arg Phe Val Ile His Ala Lys Ser
            20                  25                  30

Glu Pro Ser Glu Lys Ser Val Glu Ile Met Arg Lys Phe Ser Glu Gln
            35                  40                  45

Tyr Ala Arg Arg Ser Gly Thr Tyr Phe Cys Val Asp Lys Gly Val Thr
    50                  55                  60

Ser Val Val Ile Lys Gly Leu Ala Glu His Lys Asp Ser Tyr Gly Ala
65                  70                  75                  80

Pro Leu Cys Pro Cys Arg His Tyr Asp Asp Lys Ala Ala Glu Val Gly
                85                  90                  95

Gln Gly Phe Trp Asn Cys Pro Cys Val Pro Met Arg Glu Arg Lys Glu
                100                 105                 110

Cys His Cys Met Leu Phe Leu Thr Pro Asp Asn Asp Phe Ala Gly Lys
            115                 120                 125

Asp Gln Thr Ile Thr Ser Glu Glu Ile Lys Glu Thr Thr Ala His Met
    130                 135                 140

<210> SEQ ID NO 97
<211> LENGTH: 146
<212> TYPE: PRT
<213> ORGANISM: Beta vulgaris
<220> FEATURE:
<221> NAME/KEY: MISC_FEATURE
<222> LOCATION: (1)..(146)
<223> OTHER INFORMATION: ferredoxin-thioredoxin reductase

<400> SEQUENCE: 97

Met Thr Met Lys Ser Leu Gln Ala Ser Thr Ala Tyr Ser Phe Pro Ile
1               5                   10                  15
```

```
Ser Ser Pro Ser Ile Ser Pro Arg Arg Phe Ser Arg Val Ile Arg Ala
            20                  25                  30

Gln Val Asp Pro Ser Glu Lys Ser Val Glu Val Met Arg Lys Phe Ser
        35                  40                  45

Glu Gln Phe Cys Arg Lys Ser Glu Thr Tyr Phe Cys Ala Asp Lys Ser
    50                  55                  60

Val Thr Ala Val Val Ile Lys Gly Leu Ala Glu His Lys Asp Thr Leu
65                  70                  75                  80

Gly Ala Pro Leu Cys Pro Cys Arg His Tyr Asp Asp Lys Ala Ala Glu
                85                  90                  95

Ala Lys Gln Gly Phe Trp Asn Cys Pro Cys Val Pro Met Arg Glu Arg
            100                 105                 110

Lys Glu Cys His Cys Met Leu Phe Leu Thr Pro Asp Asn Asp Phe Ala
        115                 120                 125

Gly Lys Asp Gln Thr Ile Ser Leu Asp Glu Ile Arg Glu Thr Thr Ala
    130                 135                 140

Asn Met
145

<210> SEQ ID NO 98
<211> LENGTH: 144
<212> TYPE: PRT
<213> ORGANISM: Raphanus sativus
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 98

Met Asn Pro Gln Ala Val Ser Cys Ser Ser Phe Gly Phe Val Ser Ala
1               5                   10                  15

Pro Leu Val Ser Pro Arg Thr Ser Arg Phe Val Ile His Ala Lys Ser
            20                  25                  30

Glu Pro Ser Glu Lys Ser Val Glu Ile Met Arg Lys Phe Ser Glu Gln
        35                  40                  45

Tyr Ala Arg Arg Ser Gly Thr Tyr Phe Cys Val Asp Lys Gly Val Thr
    50                  55                  60

Ser Val Val Ile Lys Gly Leu Ala Glu His Lys Asp Ser Tyr Gly Ala
65                  70                  75                  80

Pro Leu Cys Pro Cys Arg His Tyr Asp Asp Lys Ala Ala Glu Val Gly
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Lys
        115                 120                 125

Asp Gln Thr Ile Thr Ser Glu Glu Ile Lys Glu Thr Thr Ala His Met
    130                 135                 140

<210> SEQ ID NO 99
<211> LENGTH: 147
<212> TYPE: PRT
<213> ORGANISM: Eutrema salsugineum
<220> FEATURE:
<221> NAME/KEY: MISC_FEATURE
<222> LOCATION: (1)..(147)
<223> OTHER INFORMATION: ferredoxin-thioredoxin reductase

<400> SEQUENCE: 99

Met Asn Leu Gln Ala Val Ser Cys Ser Phe Gly Cys Ala Ser Cys Val
```

```
                1               5                   10                  15
            Ser Leu His Ser Tyr Lys Ala Ser Phe Arg Arg Ser Phe Thr Ile Arg
                            20                  25                  30
            Ala Lys Ser Glu Pro Ser Glu Lys Ser Ile Glu Ile Met Arg Lys Phe
                            35                  40                  45
            Ser Glu Gln Tyr Ala Arg Arg Ser Gly Thr Tyr Phe Cys Val Asp Lys
                50                      55                  60
            Gly Val Thr Ser Val Val Ile Lys Gly Leu Ala Glu His Lys Asp Ser
             65                     70                  75                  80
            Tyr Gly Ala Pro Leu Cys Pro Cys Arg His Tyr Asp Asp Lys Ala Ala
                            85                  90                  95
            Glu Val Gly Gln Gly Phe Trp Asn Cys Pro Cys Val Pro Met Arg Glu
                            100                 105                 110
            Arg Lys Glu Cys His Cys Met Leu Phe Leu Thr Pro Asp Asn Asp Phe
                            115                 120                 125
            Ala Gly Lys Asp Gln Thr Ile Thr Ser Glu Glu Ile Lys Glu Thr Thr
                130                     135                 140
            Ala Asn Met
            145

<210> SEQ ID NO 100
<211> LENGTH: 144
<212> TYPE: PRT
<213> ORGANISM: Phalaenopsis equestris
<220> FEATURE:
<221> NAME/KEY: MISC_FEATURE
<222> LOCATION: (1)..(144)
<223> OTHER INFORMATION: ferredoxin-thioredoxin reductase

<400> SEQUENCE: 100

Met Ser Ile Gln Ser Ser Phe Ala Gly Ala Ala Leu Pro Leu Pro Val
             1              5                   10                  15
            Ala Val Pro Pro Gln Arg Arg Cys Leu Gly Leu Ile Arg Ala Lys Val
                            20                  25                  30
            Glu Pro Ser Glu Lys Ser Val Glu Ile Met Arg Lys Phe Ser Glu Gln
                            35                  40                  45
            Tyr Ala Arg Arg Ser Glu Thr Tyr Phe Cys Val Asp Lys Gly Val Thr
                50                      55                  60
            Ser Val Val Ile Lys Gly Leu Ala Asp His Lys Glu Thr Leu Gly Ala
             65                     70                  75                  80
            Pro Leu Cys Pro Cys Arg His Tyr Asp Asp Lys Ala Ala Glu Ala Ala
                            85                  90                  95
            Gln Gly Phe Trp Asn Cys Pro Cys Val Pro Met Arg Glu Arg Lys Glu
                            100                 105                 110
            Cys His Cys Met Leu Phe Leu Thr Pro Asp Asn Asp Phe Ala Gly Arg
                            115                 120                 125
            Glu Gln Thr Ile Thr Leu Asp Glu Ile Lys Leu Ser Thr Ser Asn Leu
                130                     135                 140

<210> SEQ ID NO 101
<211> LENGTH: 149
<212> TYPE: PRT
<213> ORGANISM: Picea sitchensis
<220> FEATURE:
<221> NAME/KEY: MISC_FEATURE
<222> LOCATION: (1)..(149)
<223> OTHER INFORMATION: ferredoxin-thioredoxin reductase

<400> SEQUENCE: 101
```

```
Met Ala Asn Ile Ala Ile Gly Leu Pro Asn Phe Ser Met Gly Cys Val
1               5                   10                  15

Tyr Lys Ser Gln His Phe Lys Asn Pro Ser Lys Arg Leu Ile Thr Val
            20                  25                  30

Arg Ala Asn Lys Val Glu Pro Ser Asp Lys Ser Val Glu Ile Met Arg
        35                  40                  45

Lys Phe Ser Glu Gln Tyr Ala Arg Arg Ser Gly Thr Tyr Phe Cys Val
    50                  55                  60

Asp Lys Ala Val Thr Ser Val Val Ile Lys Gly Leu Ala Glu His Lys
65                  70                  75                  80

Asp Thr Leu Gly Ala Pro Leu Cys Pro Cys Arg His Tyr Asp Asp Lys
                85                  90                  95

Val Thr Glu Ala Lys Gln Gly Phe Trp Asn Cys Pro Cys Val Pro Met
            100                 105                 110

Arg Glu Arg Lys Glu Cys His Cys Met Leu Phe Leu Thr Pro Asp Asn
        115                 120                 125

Asp Phe Ala Gly Lys Asp Gln Gly Ile Ser Ser Glu Glu Met Lys Glu
    130                 135                 140

Leu Thr Val Asn Phe
145

<210> SEQ ID NO 102
<211> LENGTH: 145
<212> TYPE: PRT
<213> ORGANISM: Gossypium arboreum
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 102

Met Thr Leu Gln Ala Thr Ser Cys Asn Phe Gly Ala Ile Ser Ser Leu
1               5                   10                  15

Leu Arg Pro Pro Lys Ile Ser Arg His Arg Phe Val Ile Arg Ala Glu
            20                  25                  30

Val Glu Pro Ser Glu Lys Ser Val Glu Ile Met Arg Lys Phe Ser Glu
        35                  40                  45

Gln Tyr Ala Arg Arg Ser Gly Thr Tyr Phe Cys Met Asp Lys Gly Val
    50                  55                  60

Thr Ser Val Val Ile Lys Gly Leu Ala Glu His Lys Asn Ser Leu Gly
65                  70                  75                  80

Ala Pro Leu Cys Pro Cys Arg His Tyr Asp Asp Lys Ala Ala Glu Ala
                85                  90                  95

Ser Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Gln Asp Gln Thr Ile Thr Leu Glu Glu Ile Lys Glu Thr Thr Ala Asn
    130                 135                 140

Met
145

<210> SEQ ID NO 103
<211> LENGTH: 144
<212> TYPE: PRT
<213> ORGANISM: Dendrobium catenatum
<220> FEATURE:
```

```
<221> NAME/KEY: MISC_FEATURE
<222> LOCATION: (1)..(144)
<223> OTHER INFORMATION: ferredoxin-thioredoxin reductase

<400> SEQUENCE: 103

Met Ser Ile Gln Ser Ser Phe Ala Gly Val Ala Leu Pro Leu Pro Val
1               5                   10                  15

Ala Val Val Pro Leu Arg Arg Ser Val Ser Leu Ile Arg Ala Lys Val
                20                  25                  30

Glu Pro Ser Glu Lys Thr Val Glu Ile Met Arg Lys Phe Ser Glu Gln
            35                  40                  45

Tyr Ala Arg Arg Ser Glu Thr Tyr Phe Cys Val Asp Lys Gly Val Thr
    50                  55                  60

Ser Val Val Ile Lys Gly Leu Ala Asp His Lys Glu Thr Leu Gly Ala
65                  70                  75                  80

Pro Leu Cys Pro Cys Arg His Tyr Asp Asp Lys Ala Ala Glu Ala Ala
                85                  90                  95

Gln Gly Phe Trp Asn Cys Pro Cys Val Pro Met Arg Glu Arg Lys Glu
            100                 105                 110

Cys His Cys Met Leu Phe Leu Thr Pro Asp Asn Asp Phe Ala Gly Arg
        115                 120                 125

Glu Gln Ser Ile Thr Leu Asp Glu Ile Lys Val Ser Thr Ser Asn Leu
    130                 135                 140

<210> SEQ ID NO 104
<211> LENGTH: 145
<212> TYPE: PRT
<213> ORGANISM: Gossypium hirsutum
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 104

Met Thr Leu Gln Ala Ser Phe Phe Asn Phe Gly Ser Ile Ser Ser Leu
1               5                   10                  15

Pro Cys Pro Pro Arg Thr Ser Arg Gln Arg Phe Val Ile Arg Ala Lys
                20                  25                  30

Val Glu Pro Ser Glu Lys Ser Val Glu Ile Met Arg Lys Phe Ser Glu
            35                  40                  45

Gln Tyr Ala Arg Arg Ser Gly Thr Tyr Phe Cys Val Asp Lys Gly Val
    50                  55                  60

Thr Ser Val Val Ile Lys Gly Leu Ala Glu His Lys Asp Thr Leu Gly
65                  70                  75                  80

Ala Pro Leu Cys Pro Cys Arg His Tyr Asp Asp Lys Ala Ala Glu Val
                85                  90                  95

Gly Gln Gly Phe Trp Asn Cys Pro Cys Val Pro Met Arg Glu Arg Lys
            100                 105                 110

Glu Cys Gly Cys Met Leu Phe Leu Thr Pro Asp Asn Asp Phe Ala Gly
        115                 120                 125

Gln Asp Gln Ala Ile Thr Leu Glu Glu Ile Lys Glu Thr Thr Ala Asn
    130                 135                 140

Met
145

<210> SEQ ID NO 105
<211> LENGTH: 145
<212> TYPE: PRT
```

<213> ORGANISM: Arabis alpina
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 105

```
Met Asn Leu Gln Ala Val Ser Cys Ser Phe Gly Ser Val Ser Val Pro
1               5                   10                  15

Leu Val Ser Pro Arg Thr Pro Phe Arg Arg Phe Val Ile Gln Ala Lys
            20                  25                  30

Ser Glu Pro Ser Glu Lys Ser Val Glu Leu Met Arg Lys Phe Ser Glu
        35                  40                  45

Gln Tyr Ala Arg Arg Ser Glu Thr Tyr Phe Cys Val Asp Lys Gly Val
    50                  55                  60

Thr Ser Val Val Ile Lys Gly Leu Ala Glu His Lys Asp Ser Tyr Gly
65                  70                  75                  80

Ala Pro Leu Cys Pro Cys Arg His Tyr Asp Asp Lys Ala Ala Glu Val
                85                  90                  95

Lys Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125

Lys Asp Gln Ser Ile Thr Leu Asp Glu Ile Lys Glu Thr Thr Ala Ser
    130                 135                 140

Met
145
```

<210> SEQ ID NO 106
<211> LENGTH: 145
<212> TYPE: PRT
<213> ORGANISM: Lupinus angustifolius
<220> FEATURE:
<221> NAME/KEY: MISC_FEATURE
<222> LOCATION: (1)..(145)
<223> OTHER INFORMATION: ferredoxin-thioredoxin reductase

<400> SEQUENCE: 106

```
Met Thr Leu Gln Ala Ser Thr Phe Ala Val Ala Ile Pro Ser Ser Ala
1               5                   10                  15

Val Thr Pro Leu Arg Arg His Arg Asn Leu Phe Thr Val Arg Ala Gln
            20                  25                  30

Val Glu Pro Thr Asp Lys Asn Val Glu Ile Met Arg Lys Phe Ser Glu
        35                  40                  45

Gln Tyr Ala Arg Lys Ser Gly Thr Tyr Phe Cys Val Asp Lys Gly Val
    50                  55                  60

Thr Ser Val Val Ile Lys Gly Leu Ala Asp His Lys Asp Ser Leu Gly
65                  70                  75                  80

Ala Pro Leu Cys Pro Cys Arg His Tyr Asp Asp Lys Pro Ala Glu Ala
                85                  90                  95

Ser Gln Gly Phe Trp Asn Cys Pro Cys Val Pro Met Arg Glu Arg Lys
            100                 105                 110

Glu Cys His Cys Met Leu Phe Leu Thr Pro Asp Asn Asp Phe Ala Gly
        115                 120                 125
```

```
Gln Glu Gln Thr Ile Thr Leu Asp Glu Ile Lys Glu Ala Thr Ala Asn
    130                 135                 140
Met
145
```

MAIZE RBCS7A PROMOTER FOR EXPRESSING A FERREDOXIN-THIOREDOXIN REDUCTASE IN A PLANT

CROSS-REFERENCE TO RELATED APPLICATIONS

This application is a national stage filing under 35 U.S.C. 371 of PCT/IB2018/055168 filed Jul. 12, 2018, which International Application was published by the International Bureau in English on Jan. 17, 2019, and application claims priority from U.S. Provisional Patent Application No. 62/532,085, filed Jul. 13, 2017, which applications are hereby incorporated in their entirety by reference in this application.

FIELD OF THE INVENTION

The invention is drawn to compositions and methods for increasing plant growth and yield through expression of a ferredoxin-thioredoxin reductase gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to precisely modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance, photosynthetic carbon assimilation rates, and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in the metabolic pathways that contribute to plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth resulting in higher crop yield. Such methods include increasing the expression of at least one ferredoxin-thioredoxin reductase gene in a plant of interest. The invention also encompasses constructs comprising a promoter that drives expression in a plant cell operably linked to a ferredoxin-thioredoxin reductase coding sequence. Compositions further comprise plants, plant seeds, plant organs, plant cells, and other plant parts that have increased expression of a ferredoxin-thioredoxin reductase sequence. The invention includes methods that can be utilized to increase expression of a ferredoxin-thioredoxin reductase gene in a plant. Such ferredoxin-thioredoxin reductase gene may be a native sequence or alternatively, may be a sequence that is heterologous to the plant of interest.

Embodiments of the invention include:
1. A method for increasing crop yield comprising transforming a plant with at least one ferredoxin-thioredoxin reductase protein-encoding sequence.
2. The method of embodiment 1, wherein said ferredoxin-thioredoxin reductase protein-encoding sequence comprises SEQ ID NO:1, or encodes a protein selected from the group of SEQ ID NOs:2 and 14-106.
3. The method of embodiment 1, wherein said ferredoxin-thioredoxin reductase protein-encoding sequence encodes a protein with at least 80%, 90%, 95%, 96%, 97%, 98%, or 99% sequence identity to a sequence selected from the group of SEQ ID NOs:2 and 14-106, and that has ferredoxin-thioredoxin reductase function.
4. The method of embodiment 1, wherein said ferredoxin-thioredoxin reductase protein-encoding sequence encodes a protein with at least 80%, 85%, 90%, 95%, 96%, 97%, 98%, or 99% sequence positives relative to a sequence selected from the group of SEQ ID NOs:2 and 14-106, and that has ferredoxin-thioredoxin reductase function.
5. A plant having stably incorporated into its genome a promoter that drives expression in a plant operably linked to a ferredoxin-thioredoxin reductase protein-encoding sequence, wherein said promoter is heterologous to said ferredoxin-thioredoxin reductase protein-encoding sequence.
6. The plant of embodiment 5, wherein said ferredoxin-thioredoxin reductase protein-encoding sequence comprises SEQ ID NO:1, or encodes a protein selected from the group of SEQ ID NOs:2 and 14-106.
7. The plant of embodiment 5, wherein said ferredoxin-thioredoxin reductase protein-encoding sequence encodes a protein with at least 80%, 85%, 90%, 95%, 96%, 97%, 98%, or 99% sequence identity to a sequence selected from the group of SEQ ID NOs:2 and 14-106, and that has ferredoxin-thioredoxin reductase function.
8. The plant of embodiment 5, wherein said ferredoxin-thioredoxin reductase protein-encoding sequence encodes a protein with at least 80%, 85%, 90%, 95%, 96%, 97%, 98%, or 99% sequence positives relative to a sequence selected from the group of SEQ ID NOs:2 and 14-106, and that has ferredoxin-thioredoxin reductase function.
9. Transformed seed of any one of the plants of embodiments 5-8.
10. The plant of any one of embodiments 5-8 wherein said plant is a monocot.
11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena,* or *Hordeum.*
12. The plant of any one of embodiments 5-8 wherein said plant is a dicot.
13. The plant of embodiment 12 wherein said plant is from the genus *Glycine, Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prunus, Beta, Populus,* or *Eucalyptus.*
14. The plant of any one of embodiments 5-8 wherein said plant exhibits increased growth relative to a control plant.
15. The plant of any one of embodiments 5-8 wherein said plant exhibits increased biomass yield relative to a control plant.
16. The plant of any one of embodiments 5-8 wherein said plant exhibits increased seed yield relative to a control plant.
17. The method of any one of embodiments 1-4, wherein said ferredoxin-thioredoxin reductase protein-encoding sequence is expressed from a developmentally regulated promoter.
18. The method of embodiment 17, wherein said developmentally regulated promoter comprises SEQ ID NO:5.
19. The method of any one of embodiments 1-18, further comprising transforming a plant with at least one additional protein-encoding sequence.
20. The method of embodiment 19 wherein said at least one additional protein-encoding sequence is selected from the group of SEQ ID NOs:8 and 11, or encodes a protein with at least 90% identity to a sequence selected from the group of SEQ ID NOs:9 and 12.
21. The method of embodiment 19 or 20 wherein said at least one additional protein-encoding sequence encodes a protein selected from the group of SEQ ID NOs:9 and 12.
22. The plant of any one of embodiments 5-8, wherein said promoter that drives expression in a plant is a developmentally regulated promoter.
23. The plant of embodiment 22, wherein said developmentally promoter comprises SEQ ID NO:5.
24. The plant of embodiment 5 having stably incorporated into its genome a second promoter that drives expression in a plant operably linked to a second protein-encoding sequence, wherein said second promoter is heterologous to said second protein-encoding sequence.
25. The plant of embodiment 24 wherein said second protein-encoding sequence is selected from the group of SEQ ID NOs:8 and 11, or encodes a protein with at least 90% identity to a sequence selected from the group of SEQ ID NOs:9 and 12.
26. The plant of embodiment 24 or 25 wherein said second protein-encoding sequence encodes a protein selected from the group of SEQ ID NOs:9 and 12.
27. A DNA construct comprising, in operable linkage,
   a. A promoter that is functional in a plant cell and,
   b. A nucleic acid sequence encoding a ferredoxin-thioredoxin reductase protein.
28. The DNA construct of embodiment 27, wherein said nucleic acid sequence encoding a ferredoxin-thioredoxin reductase protein comprises SEQ ID NO:1, or encodes a protein selected from the group consisting of SEQ ID NOs:2 and 14-106.
29. The DNA construct of embodiment 27 or 28, wherein said nucleic acid sequence encoding a ferredoxin-thioredoxin reductase protein encodes a protein with at least 80%, 85%, 90%, 95%, 96%, 97%, 98%, or 99% sequence identity to a sequence selected from the group of SEQ ID NOs:2 and 14-106, and that has ferredoxin-thioredoxin reductase function.
30. The DNA construct of embodiment 27 or 28, wherein said nucleic acid sequence encoding a ferredoxin-thioredoxin reductase protein encodes a protein with at least 80%, 85%, 90%, 95%, 96%, 97%, 98%, or 99% sequence positives relative to a sequence selected from the group of SEQ ID NOs:2 and 14-106, and that has ferredoxin-thioredoxin reductase function.
31. The DNA construct of embodiment 27 or 28, wherein said promoter that is functional in a plant cell comprises SEQ ID NO:5.
32. The DNA construct of any one of embodiments 27-31, wherein said promoter is heterologous to said nucleic acid sequence encoding a ferredoxin-thioredoxin reductase protein.
33. A method for increasing crop yield comprising modulating the expression of at least one ferredoxin-thioredoxin reductase protein-encoding sequence in a plant.
34. The method of embodiment 33 wherein said modulating the expression comprises increasing the expression of at least one ferredoxin-thioredoxin reductase protein-encoding sequence in a plant.
35. The method of embodiment 34, wherein said increasing the expression comprises increasing the activity of a native ferredoxin-thioredoxin reductase sequence in said plant or increasing activity of a native ferredoxin-thioredoxin reductase protein-encoding sequence in said plant.
36. The plant of any one of embodiments 5-8, wherein said promoter that drives expression in a plant is active in leaf tissue.
37. The DNA construct of any one of embodiments 27-32, wherein said promoter that is functional in a plant cell is active in leaf tissue.

DETAILED DESCRIPTION OF THE INVENTION

Compositions and methods for increasing crop biomass and yield are provided. The methods include increasing the expression of at least one ferredoxin-thioredoxin reductase gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found below-ground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding a ferredoxin-thioredoxin reductase protein. In a preferred embodiment, the expression of a ferredoxin-thioredoxin reductase protein-encoding gene is upregulated relative to ferredoxin-thioredoxin reductase expression levels in a control plant, resulting in increased harvestable biomass in plants with increased ferredoxin-thioredoxin reductase expression relative to control plants. Any methods for increasing the activity or expression of a ferredoxin-thioredoxin reductase protein-encoding sequence in a plant are encompassed by the present invention.

The compositions of the invention include constructs comprising the coding sequence set forth in SEQ ID NO:1 or encoding a protein selected from the group of SEQ ID NOs:2 and 14-106 or variants thereof, operably linked to a promoter that is functional in a plant cell. By "promoter" is intended to mean a regulatory region of DNA that is capable of driving expression of a sequence in a plant or plant cell. It is recognized that having identified the ferredoxin-thioredoxin reductase protein sequences disclosed herein, it is within the state of the art to isolate and identify additional ferredoxin-thioredoxin reductase protein sequences and nucleotide sequences encoding ferredoxin-thioredoxin reductase protein sequences, for instance through BLAST searches, PCR assays, and the like.

The coding sequences of the present invention, when assembled within a DNA construct such that a promoter is operably linked to the coding sequence of interest, enable expression and accumulation of ferredoxin-thioredoxin reductase protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the ferredoxin-thioredoxin reductase proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the ferredoxin-thioredoxin reductase protein-encoding nucleotide sequence. While the ferredoxin-thioredoxin reductase protein-encoding nucleotide sequence and the promoter sequence are heterologous to each other, either the ferredoxin-thioredoxin reductase protein-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain ferredoxin-thioredoxin reductase function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as the conversion of reduced ferredoxin to reduced thioredoxin to regulate enzyme activity. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

Classes of Amino Acids

| Amino Acid Class | Example Amino Acids |
| --- | --- |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the world wide web at ncbi.nlm.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding ferredoxin-thioredoxin reductase proteins, i.e. upregulating expression. Likewise, in some instances, plant growth and yield may be increased by decreasing the expression levels of one or more genes encoding ferredoxin-thioredoxin reductase proteins, i.e. downregulating expression. Thus, the invention encompasses the upregulation or downregulation of one or more genes encoding ferredoxin-thioredoxin reductase proteins. Further, the methods include the upregulation of at least one gene encoding a ferredoxin-thioredoxin reductase protein and the downregulation of at least one gene encoding a second ferredoxin-thioredoxin reductase protein in a plant of interest. By modulating the concentration and/or activity of at least one of the genes encoding a ferredoxin-thioredoxin reductase protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding ferredoxin-thioredoxin reductase proteins of the present invention can be controlled by the use of one or more promoters that are functional in a plant cell. The expression level of the ferredoxin-thioredoxin reductase protein-encoding gene of interest may be measured directly, for example, by assaying for the level of the ferredoxin-thioredoxin reductase gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. ferredoxin-thioredoxin reductase function can be assessed by, for example, assessing activation of NADP-MDH in reconstituted thylakoids (Droux et al. (1987) *Arch Biochem Biophys* 252:426-439.

A "subject plant or plant cell" is one in which genetic alteration, such as transformation, has been effected as to a ferredoxin-thioredoxin reductase protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of a ferredoxin-thioredoxin reductase protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of a ferredoxin-thioredoxin reductase protein-encoding gene of interest, antisense constructions, complementary to at least a portion of the messenger RNA (mRNA) for the sequences of a gene of interest, particularly a gene encoding a ferredoxin-thioredoxin reductase protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding ferredoxin-thioredoxin reductase proteins can be identified and used in the methods of the invention. The variant sequences will retain the biological activity of a ferredoxin-thioredoxin reductase protein (i.e., catalyzing the conversion of reduced ferredoxin to reduced thioredoxin to regulate enzyme activity). The present invention shows that, unexpectedly, certain novel expression strategies for ferredoxin-thioredoxin reductase protein overexpression can lead to increased biomass and seed yield.

The expression cassette will include in the 5'-3' direction of transcription, a transcriptional and translational initiation region, a polynucleotide encoding a ferredoxin-thioredoxin reductase protein of the present invention, and a transcriptional and translational termination region (i.e., termination region) functional in plants.

A number of promoters may be used in the practice of the invention. The polynucleotides encoding a ferredoxin-thioredoxin reductase protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding ferredoxin-thioredoxin reductase proteins of the invention may be expressed from tissue-preferred promoters. Tissue-preferred promoters include Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Developmentally-regulated promoters may be desirable for the expression of a polynucleotide encoding a ferredoxin-thioredoxin reductase protein. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding a ferredoxin-thioredoxin reductase protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding a ferredoxin-thioredoxin reductase protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding ferredoxin-thioredoxin reductase proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477;

Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), quinoa (*Chenopodium quinoa*), chicory (*Cichorium intybus*), lettuce (*Lactuca sativa*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding a ferredoxin-thioredoxin reductase protein of the present invention is used to transform a plant cell or cells. The transformed plant cell or cells are regenerated to produce transformed plants. These plants transformed with a construct comprising a functional promoter driving expression of a ferredoxin-thioredoxin reductase protein-encoding polynucleotide of the invention demonstrated increased plant yield, i.e., increased above-ground biomass and/or and/or increased harvestable biomass and/or increased seed yield.

Now that it has been demonstrated that upregulation of ferredoxin-thioredoxin reductase increases plant yield, other methods for increasing expression of an endogenous ferredoxin-thioredoxin reductase sequence in a plant of interest can be used. The expression of a ferredoxin-thioredoxin reductase gene present in a plant's genome can be altered by inserting a transcriptional enhancer upstream of the ferredoxin-thioredoxin reductase gene present in the plant's genome. This strategy will allow the ferredoxin-thioredoxin reductase gene's expression to retain its normal developmental profile, while showing elevated transcript levels. This strategy will occur through the insertion of an enhancer element upstream of a ferredoxin-thioredoxin reductase gene of interest using a meganuclease designed against the genomic sequence of interest. Alternatively, a Cas9 endonuclease coupled with a guide RNA (gRNA) designed against the genomic sequence of interest, or a Cpf1 endonuclease coupled with a gRNA designed against the genomic sequence of interest, or a Csm1 endonuclease coupled with a gRNA designed against the genomic sequence of interest is used to effect the insertion of an enhancer element upstream of a ferredoxin-thioredoxin reductase gene of interest. Alternatively, a deactivated endonuclease (e.g., a deactivated Cas9, Cpf1, or Csm1 endonuclease) fused to a transcriptional enhancer element is targeted to a genomic location near the transcription start site for a ferredoxin-thioredoxin reductase gene of interest, thereby modulating the expression of said ferredoxin-thioredoxin reductase gene of interest (Piatek et al. (2015) *Plant Biotechnol J* 13:578-589).

Modulation of the expression of a ferredoxin-thioredoxin reductase protein-encoding gene may be achieved through the use of precise genome-editing technologies to modulate the expression of the endogenous sequence. In this manner, a nucleic acid sequence will be inserted proximal to a native plant sequence encoding the ferredoxin-thioredoxin reductase through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163:759-771, U.S. Provisional Patent Application 62/295,325); *N. gregoryi* Argonaute-mediated DNA insertion (Gao et al. (2016) *Nat Biotechnol doi:*10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cal et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression, decreased expression, and/or altered expression profile of a ferredoxin-thioredoxin reductase gene.

Enhancers include any molecule capable of enhancing gene expression when inserted into the genome of a plant. Thus, an enhancer can be inserted in a region of the genome upstream or downstream of a ferredoxin-thioredoxin reductase sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding a ferredoxin-thioredoxin reductase protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of ferredoxin-thioredoxin reductase gene expression may also be achieved through the modification of DNA in a way that does not alter the sequence of the DNA. Such changes could include modifying the chromatin content or structure of the ferredoxin-thioredoxin reductase gene of interest and/or of the DNA surrounding the ferredoxin-thioredoxin reductase gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the ferredoxin-thioredoxin reductase gene of interest and/or of the DNA surrounding the ferredoxin-thioredoxin reductase gene of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the ferredoxin-thioredoxin reductase gene of interest may be applied in order to achieve the desired result of an altered ferredoxin-thioredoxin reductase gene expression profile.

Alteration of ferredoxin-thioredoxin reductase gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding a ferredoxin-thioredoxin reductase may be achieved by inserting a transposable element upstream of the ferredoxin-thioredoxin reductase gene of interest, causing the expression of said gene to be altered.

Alteration of ferredoxin-thioredoxin reductase gene expression may also be achieved through expression of a transcription factor or transcription factors that regulate the expression of the ferredoxin-thioredoxin reductase gene of interest. It is well understood that alteration of transcription factor expression can in turn alter the expression of the target gene(s) of said transcription factor (Hiratsu et al. (2003) *Plant J* 34:733-739). Alteration of ferredoxin-thioredoxin reductase gene expression may be achieved by altering the expression of transcription factor(s) that are known to interact with a ferredoxin-thioredoxin reductase gene of interest.

Alteration of ferredoxin-thioredoxin reductase gene expression may also be achieved through the insertion of a promoter upstream of the open reading frame encoding a native ferredoxin-thioredoxin reductase in the plant species of interest. This will occur through the insertion of a promoter of interest upstream of a ferredoxin-thioredoxin reductase protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-cpf1, CRISPR-Csm1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of Ferredoxin-Thioredoxin Reductase Plant Transformation Vectors An open reading frame encoding a maize ferredoxin-thioredoxin reductase protein was synthesized. This open reading frame comprised SEQ ID NO:1, encoding the protein sequence of SEQ ID NO:2. Appropriate restriction sites were included at the 5' and 3' ends of the coding sequence to allow this DNA to be cloned into plant transformation vectors that contained genetic elements suitable for controlling gene expression. In each plant transformation construct, the ferredoxin-thioredoxin reductase open reading frame was located downstream of a plant promoter and 5' untranslated region (5'UTR) and upstream of a 3'UTR. Table 2 summarizes the plant transformation constructs that were built containing a ferredoxin-thioredoxin reductase open reading frame.

TABLE 2

Ferredoxin-thioredoxin reductase plant transformation constructs

| Construct | Promoter + 5'UTR | ORF | 3'UTR |
|---|---|---|---|
| 131361 | 2x35S (SEQ ID NO: 3) | GRMZM2G122793 (SEQ ID NO: 1, encoding SEQ ID NO: 2) | 35S poly A (SEQ ID NO: 4) |
| 131362 | RbcS7A (SEQ ID NO: 5) | GRMZM2G122793 (SEQ ID NO: 1, encoding SEQ ID NO: 2) | ZmRbcS (SEQ ID NO: 6) |
| 132263 | RbcS7A (SEQ ID NO: 5) | GRMZM2G122793 (SEQ ID NO: 1, encoding SEQ ID NO: 2) | ZmRbcS (SEQ ID NO: 6) |

In addition to the single-genic ferredoxin-thioredoxin reductase plant transformation constructs listed in Table 2, multigenic plant transformation constructs containing a ferredoxin-thioredoxin reductase gene cassette and a second linked cassette were also built. Table 3 summarizes the multigenic ferredoxin-thioredoxin reductase plant transformation constructs.

TABLE 3

Ferredoxin-thioredoxin reductase multigenic plant transformation constructs

| Construct | Promoter + 5'UTR | ORF | 3'UTR | Promoter + 5'UTR2 | ORF2 | 3'UTR2 |
|---|---|---|---|---|---|---|
| 132307 | RbcS7A (SEQ ID NO: 5) | GRMZM2G122793 (SEQ ID NO: 1, encoding SEQ ID NO: 2) | ZmRbcS (SEQ ID NO: 6) | ZmRbcS (SEQ ID NO: 7) | RbcS-ictB (SEQ ID NO: 8, encoding SEQ ID NO: 9) | ZmRbcS (SEQ ID NO: 6) |
| 132308 | RbcS7A (SEQ ID NO: 5) | GRMZM2G122793 (SEQ ID NO: 1, encoding SEQ ID NO: 2) | ZmRbcS (SEQ ID NO: 6) | 4xRGCGR (SEQ ID NO: 10) | GRMZM2G181258 (SEQ ID NO: 11, encoding SEQ ID NO: 12) | ZmCA1 (SEQ ID NO: 13) |
| 132689 | RbcS7A (SEQ ID NO: 5) | GRMZM2G122793 (SEQ ID NO: 1, encoding SEQ ID NO: 2) | ZmRbcS (SEQ ID NO: 6) | 4xRGCGR (SEQ ID NQ: 10) | GRMZM2G181258 (SEQ ID NO: 11, encoding SEQ ID NO: 12) | ZmCA1 (SEQ ID NO: 13) |

In addition to the gene cassettes described in Tables 2 and 3, each plant transformation construct listed in Tables 2 and 3 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Tables 2 and 3 contained the desired sequences, they were transformed into *A. tumefaciens* cells for plant transformation.

Example 2—Transformation of Setaria viridis

*A. tumefaciens* cells harboring ferredoxin-thioredoxin reductase plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 4 summarizes the transformation constructs used to transform *S. viridis*, along with the number of PCR-verified transgenic plants that resulted from transformation with each construct.

TABLE 4

Summary of *S. viridis* transformation with ferredoxin-thioredoxin reductase plant transformation vectors

| Construct | # Events |
|---|---|
| 131361 | 37 |
| 131362 | 31 |
| 132307 | 9 |
| 132308 | 11 |

Example 3—Transformation of Maize (*Zea mays*)

*A. tumefaciens* cells harboring ferredoxin-thioredoxin reductase plant transformation vectors are used to transform maize (*Zea mays* cv. B104) cells suitable for regeneration on tissue culture medium. Following transformation of the maize cells with the relevant plant transformation vectors and regeneration of maize plants, PCR analyses are performed to confirm the presence of the gene(s) of interest in the maize genome.

Example 4—Transformation of Rice (*Oryza sativa*)

*A. tumefaciens* cells harboring ferredoxin-thioredoxin reductase plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic *S. viridis*

Following the transformation and regeneration of *S. viridis* plants transformed with a ferredoxin-thioredoxin reductase plant transformation vector, the T0-generation plants were cultivated to maturity to produce T1-generation seeds. T1-generation *S. viridis* plants harboring the ferredoxin-thioredoxin reductase gene cassette of interest were grown in a greenhouse setting to assess the effects of ferredoxin-thioredoxin reductase gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 5 summarizes the results of the biomass and seed yield determinations made from experiments with T1-generation S. viridis plants harboring a ferredoxin-thioredoxin reductase gene cassette as a result of transformation. This table indicates the construct used for transformation, as described in Table 2, followed by the T0 event number from which the T1 seed was harvested.

TABLE 5

Summary of S. viridis greenhouse observations with T1-generation plants

| Event | DW (g) | Seed Yield (g) | DW Change | Seed Change |
| --- | --- | --- | --- | --- |
| 131361.12 | 3.35 ± 0.30 | 0.90 ± 0.13 | −16.0% | −19.4% |
| 131361.15 | 3.58 ± 0.37 | 0.99 ± 0.16 | −10.3% | −11.4% |
| 131361.18 | 4.32 ± 0.14 | 1.15 ± 0.08 | 8.3% | 2.3% |
| 131361.21 | 4.08 ± 0.46 | 1.06 ± 0.14 | 2.3% | −5.2% |
| 131361.23 | 4.00 ± 0.32 | 1.14 ± 0.12 | 0.4% | 2.2% |
| 131361.Null | 3.99 ± 0.13 | 1.12 ± 0.07 | n/a | n/a |
| 131362.10 | 3.59 ± 0.21 | 1.04 ± 0.11 | 5.2% | 11.2% |
| 131362.24 | 4.18 ± 0.20 | 1.29 ± 0.09 | 22.4% | 37.4% |
| 131362.29 | 2.59 ± 0.48 | 0.60 ± 0.15 | −24.1% | −35.3% |
| 131362.31 | 4.17 ± 0.24 | 1.15 ± 0.08 | 22.1% | 22.9% |
| 131362.Null | 3.41 ± 0.51 | 0.93 ± 0.17 | n/a | n/a |
| 132308-2 | 3.88 ± 0.45 | 0.94 ± 0.14 | −9.3% | −21.0% |
| 132308-3 | 4.33 ± 0.71 | 1.41 ± 0.07 | 1.2% | 18.5% |
| 132308-6 | 4.46 ± 0.15 | 1.42 ± 0.07 | 4.2% | 19.3% |
| 132308-null | 4.28 ± 0.12 | 1.19 ± 0.07 | n/a | n/a |

In Table 5, the dry weight of the above-ground biomass is indicated in the DW column in grams. Similarly, the dry weight of the harvested seeds is indicated in grams in the Seed Yield column. The DW Change and Seed Change columns indicate the percent change in above-ground biomass and seed yield, respectively, relative to the null segregants from the 131220 construct. As this table shows, three out of five events from the 131361 construct showed increased dry weight (0.4-8.3% increases), while two out of five events from the 131361 construct showed increased seed yield relative to null controls. Three of the four events tested from the 131362 construct showed increases in both dry weight and seed yield. Two of the three events tested from the 132308 construct showed increases in both dry weight and seed yield.

Example 6—Characterization of Transgenic Maize

T0-generation maize plants transformed with the ferredoxin-thioredoxin reductase plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the ferredoxin-thioredoxin reductase gene cassette and any other relevant gene cassettes (e.g., a selectable marker gene cassette) that were included in the ferredoxin-thioredoxin reductase plant transformation vector. Following the maturation of the maize plants, the seed is harvested. Seeds from the plants containing the ferredoxin-thioredoxin reductase gene cassette are pooled, as are seeds from the null segregant plants lacking the ferredoxin-thioredoxin reductase gene cassette. The seeds are weighed, and seed yields are calculated for the plants containing the ferredoxin-thioredoxin reductase gene cassette as well as for the null segregant plants lacking the ferredoxin-thioredoxin reductase gene cassette. Appropriate statistical analyses are performed to determine whether plants containing a ferredoxin-thioredoxin reductase gene cassette produce higher yields than those plants that lack a ferredoxin-thioredoxin reductase gene cassette.

Alternatively, T0-generation maize plants transformed with the ferredoxin-thioredoxin reductase plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the ferredoxin-thioredoxin reductase gene cassette are pooled, as are seeds from the null segregant plants lacking the ferredoxin-thioredoxin reductase gene cassette. The seeds are weighed, and seed yields are calculated for the plants containing the ferredoxin-thioredoxin reductase gene cassette as well as for the null segregant plants lacking the ferredoxin-thioredoxin reductase gene cassette. Appropriate statistical analyses are performed to determine whether plants containing a ferredoxin-thioredoxin reductase gene cassette produce higher yields than those plants that lack a ferredoxin-thioredoxin reductase gene cassette.

Example 7—Characterization of Transgenic Rice

T0-generation rice plants transformed with the ferredoxin-thioredoxin reductase plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing a ferredoxin-thioredoxin reductase gene cassette produce higher yields than those plants that lack a ferredoxin-thioredoxin reductase gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing a ferredoxin-thioredoxin reductase gene cassette produce higher yields than those plants that lack a ferredoxin-thioredoxin reductase gene cassette.

I claim:

1. A method for increasing crop yield comprising transforming a plant with at least one ferredoxin-thioredoxin reductase protein-encoding sequence, wherein said ferredoxin-thioredoxin reductase protein-encoding sequence encodes a protein comprising an amino acid sequence having at least 90% sequence identity to a selected from the group consisting of SEQ ID NOs:2 and 14-106, wherein said protein has ferredoxin-thioredoxin reductase activity; and
   wherein said ferredoxin-thioredoxin reductase protein-encoding sequence is operably linked to a promoter comprising the nucleic acid sequence set forth SEQ ID NO: 5.

2. The method of claim 1, wherein said ferredoxin-thioredoxin reductase protein-encoding sequence encodes a protein selected from the group consisting of SEQ ID NOs:2 and 14-106.

3. A plant having stably incorporated into its genome a promoter that drives expression in a plant operably linked to a ferredoxin-thioredoxin reductase protein-encoding sequence, wherein said promoter is heterologous to said ferredoxin-thioredoxin reductase protein-encoding sequence, wherein said ferredoxin-thioredoxin reductase protein-encoding sequence encodes a protein comprising an amino acid sequence having at least 90% sequence identity to a selected from the group consisting of SEQ ID NOs:2 and 14-106, wherein said protein has ferredoxin-thioredoxin reductase activity; and
   wherein said promoter comprises the nucleic acid sequence set forth SEQ ID NO: 5.

4. The plant of claim 3, wherein said ferredoxin-thioredoxin reductase protein-encoding sequence encodes a protein selected from the group consisting of SEQ ID NOs:2 and 14-106.

5. Transformed seed of the plant of claim 3, wherein said transformed seed comprises said ferredoxin-thioredoxin reductase protein-encoding sequence operably linked to said promoter.

6. The plant of claim 3 wherein said plant is a monocot.

7. The plant of claim 3 wherein said plant is a dicot.

8. A DNA construct comprising, in operable linkage,
   a. A promoter that is functional in a plant cell, wherein said promoter comprises the nucleic acid sequence set forth SEQ ID NO: 5; and,
   b. A nucleic acid sequence encoding a ferredoxin-thioredoxin reductase protein, wherein said nucleic acid sequence encoding a ferredoxin-thioredoxin reductase protein encodes a protein comprising an amino acid sequence having at least 90% sequence identity to a selected from the group consisting of SEQ ID NOs:2 and 14-106, wherein said protein has ferredoxin-thioredoxin reductase activity.

9. The DNA construct of claim 8, wherein said nucleic acid sequence encoding a ferredoxin-thioredoxin reductase protein comprises SEQ ID NO:1, or encodes a protein selected from the group consisting of SEQ ID NOs:2 and 14-106.

10. The method of claim 1, wherein said ferredoxin-thioredoxin reductase protein-encoding sequence comprises a nucleic acid sequence having at least 90% identity to the sequence set forth in SEQ ID NO:1, and encodes a protein having ferredoxin-thioredoxin reductase activity.

11. The method of claim 1, wherein said ferredoxin-thioredoxin reductase protein-encoding sequence comprises SEQ ID NO:1.

12. The plant of claim 3, wherein said ferredoxin-thioredoxin reductase protein-encoding sequence comprises a nucleic acid sequence having at least 90% identity to the sequence set forth in SEQ ID NO:1, and encodes a protein having ferredoxin-thioredoxin reductase activity.

13. The plant of claim 3, wherein said ferredoxin-thioredoxin reductase protein-encoding sequence comprises SEQ ID NO:1.

14. The DNA construct of claim 8, wherein said nucleic acid sequence encoding a ferredoxin-thioredoxin reductase protein comprises a nucleic acid sequence having at least 90% identity to the sequence set forth in SEQ ID NO:1, and encodes a protein having ferredoxin-thioredoxin reductase activity.

15. The DNA construct of claim 8, wherein said nucleic acid sequence encoding a ferredoxin-thioredoxin reductase protein comprises SEQ ID NO:1.

* * * * *

UNITED STATES PATENT AND TRADEMARK OFFICE
CERTIFICATE OF CORRECTION

PATENT NO. : 11,279,942 B2
APPLICATION NO. : 16/629754
DATED : March 22, 2022
INVENTOR(S) : Matthew Begemann It is certified that error appears in the above-identified patent and that said Letters Patent is hereby corrected as shown below:

In the Claims

At Column 136, Claim 9, Line 23, the text "protein comprises SEQ ID NO:1, or encodes a protein" should be changed to -- protein encodes a protein --.

Signed and Sealed this
Fifth Day of July, 2022

Katherine Kelly Vidal
Director of the United States Patent and Trademark Office